United States Patent
Luthra et al.

(10) Patent No.: US 10,201,625 B2
(45) Date of Patent: Feb. 12, 2019

(54) RADIOLABELLED OCTREOTATE ANALOGUES AS PET TRACERS

(75) Inventors: Sajinker Kaur Luthra, Amersham (GB); Julius Leyton, London (GB); Eric Ofori Aboagye, London (GB); Lisa Iddon, London (GB); Bard Indrevoll, Oslo (NO); Matthias Eberhard Glaser, Amersham (GB); Alan Cuthbertson, Oslo (NO)

(73) Assignees: IMPERIAL COLLEGE, London (GB); GE HEALTHCARE LIMITED, Little Chalfont (GB)

( * ) Notice: Subject to any disclaimer, the term of this patent is extended or adjusted under 35 U.S.C. 154(b) by 0 days.

(21) Appl. No.: 14/002,168

(22) PCT Filed: Mar. 1, 2012

(86) PCT No.: PCT/US2012/027168
§ 371 (c)(1),
(2), (4) Date: Aug. 29, 2013

(87) PCT Pub. No.: WO2012/118909
PCT Pub. Date: Sep. 7, 2012

(65) Prior Publication Data
US 2013/0343990 A1    Dec. 26, 2013

Related U.S. Application Data

(60) Provisional application No. 61/447,785, filed on Mar. 1, 2011.

(51) Int. Cl.
| | | |
|---|---|---|
| *A61K 51/00* | (2006.01) | |
| *A61M 36/14* | (2006.01) | |
| *A61K 51/08* | (2006.01) | |
| *C07B 59/00* | (2006.01) | |

(52) U.S. Cl.
CPC ............ *A61K 51/08* (2013.01); *A61K 51/083* (2013.01); *A61K 51/088* (2013.01); *C07B 59/002* (2013.01); *C07B 59/008* (2013.01)

(58) Field of Classification Search
CPC .... A61K 51/08; A61K 51/083; A61K 51/088; C07B 59/002; C07B 59/008
USPC ...................................................... 424/1.69
See application file for complete search history.

(56) References Cited

U.S. PATENT DOCUMENTS

| | | | | |
|---|---|---|---|---|
| 5,432,288 | A * | 7/1995 | Gerzon ................. | C07F 5/022 548/304.1 |
| 2006/0067886 | A1* | 3/2006 | Hoffman et al. | ............ 424/1.69 |
| 2009/0311177 | A1* | 12/2009 | Arstad et al. | ................ 424/1.69 |

FOREIGN PATENT DOCUMENTS

WO    WO 2009138501 A1 * 11/2009

OTHER PUBLICATIONS

Schmidt et al. J. Nucl. Med. 2004, 45, 1542-1548.*
Anderson et al. J. Nucl. Med. 2001, 42, 213-221.*
Wester et al. Eur. J. Nucl. Med. 2003, 30, 117-122.*
Glaser, et.al. Journal of Labelled Compounds and Radiopharmaceuticals, 2009, vol. 52, No. 10 pp. 407-414.
Schottelius, et.al. Clinical Cancer Research, The Americans Association for Canser Research vol. 10, No. 1, Jun. 1, 2004 pp. 3593-3606.
Schirrmacher, et.al. Tetrahaedron Letters, vol. 52, No. 15 Feb. 15, 2011, pp. 1973-1976.
Schirrmacher, et.al. Angewandte Chemie. Internation Edition, Viley VCH, Verlag, Weinheim vol. 45. No. 36, Sep. 11, 2006 pp. 6047-6050.
Wangler, et.al. Bioorganic and Medicinal Chemistry, vol. 19, No. 12, Dec. 30, 2010, pp. 3864-3874.
Idon, et.al. Bioorgranic & Medicinal Chemistry Letters, vol. 21, No. 10, Mar. 10, 2011, pp. 3122-3127.
PCT/US2012/027168 ISRWO dated Jun. 27, 2012.

* cited by examiner

*Primary Examiner* — Michael G. Hartley
*Assistant Examiner* — Sean R Donohue
(74) *Attorney, Agent, or Firm* — Mahreen Chaudhry Hoda; Carolyn S. Elmore; Elmore Patent Law Group, P.C.

(57) ABSTRACT

Novel radiotracer(s) for Positron Emission Tomography (PET) imaging are described. Novel radiotracer(s) for Positron Emission Tomography (PET) imaging of neuorendocrine tumors are described. Specifically the present invention describes novel [18F]Fluoroethyltriazol-[Tyr3] Octreotate analogs; in particular those that target somatostatin receptors found on the cell surface of gastroenteropancreatic neuorendocrine tumors. The present invention also describes intermediate(s), precursor(s), pharmaceutical composition(s), methods of making, and methods of use of the novel radiotracer(s).

9 Claims, 19 Drawing Sheets

FIG. 2
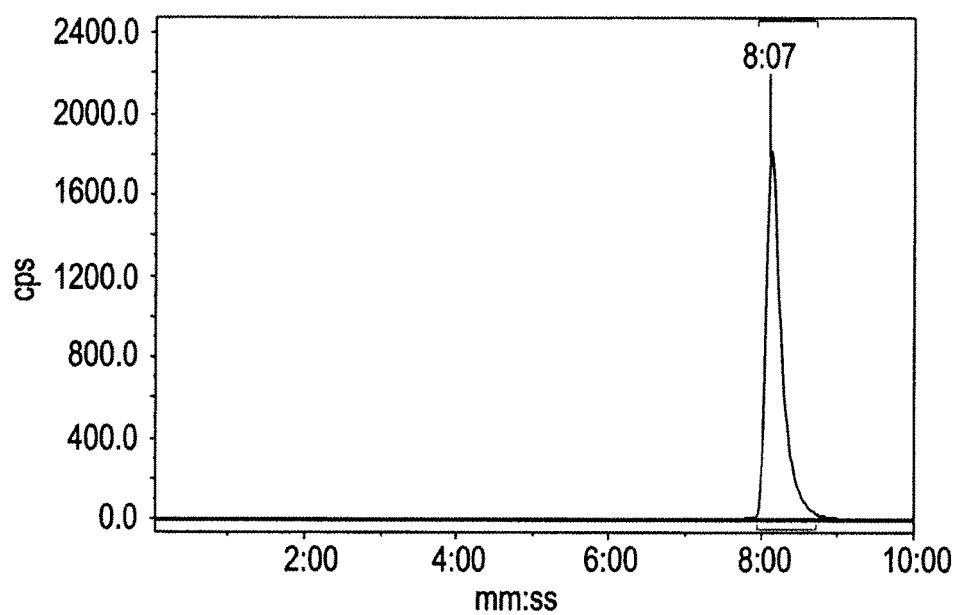
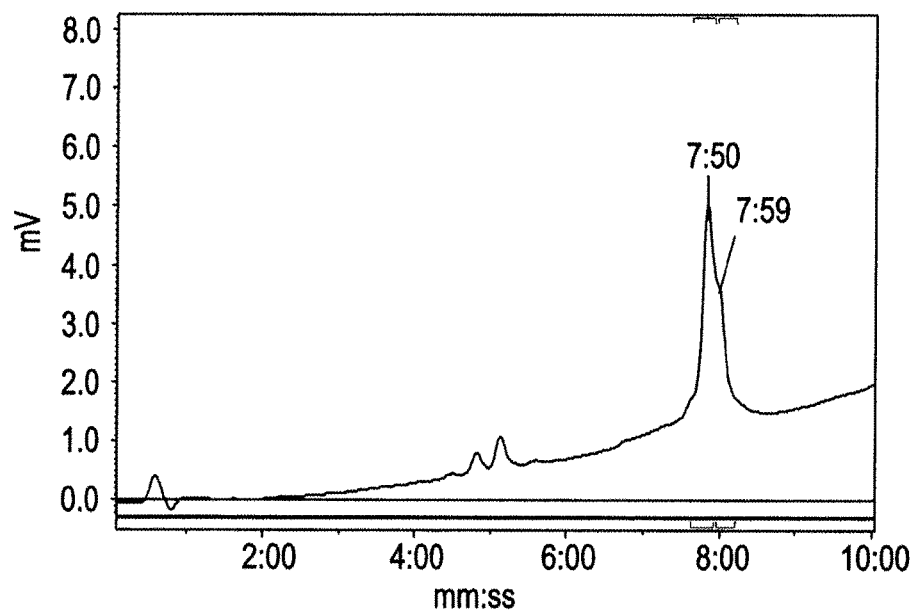

FIG. 4
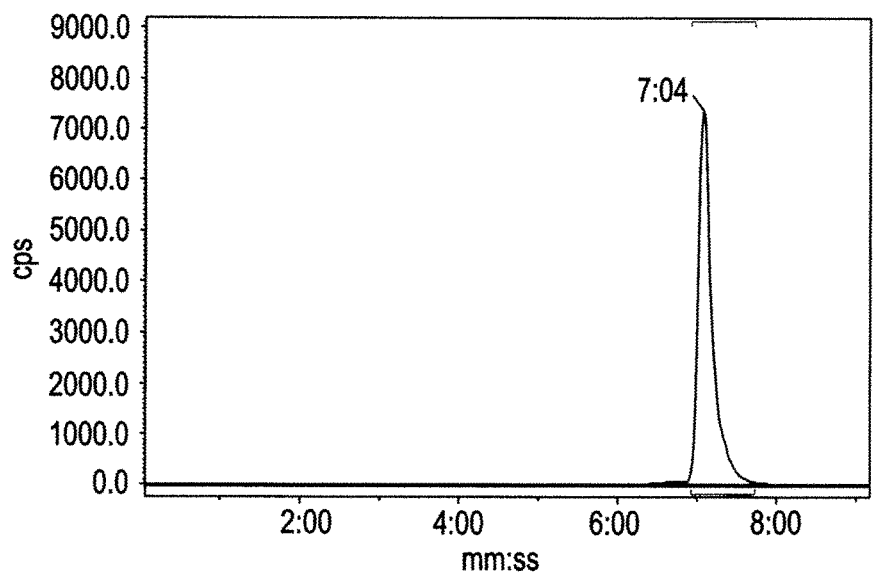
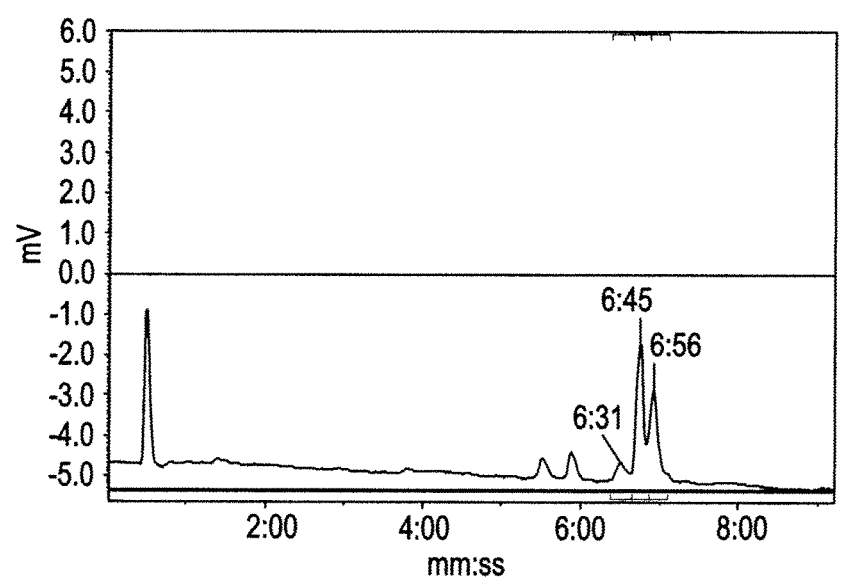

FIG. 5
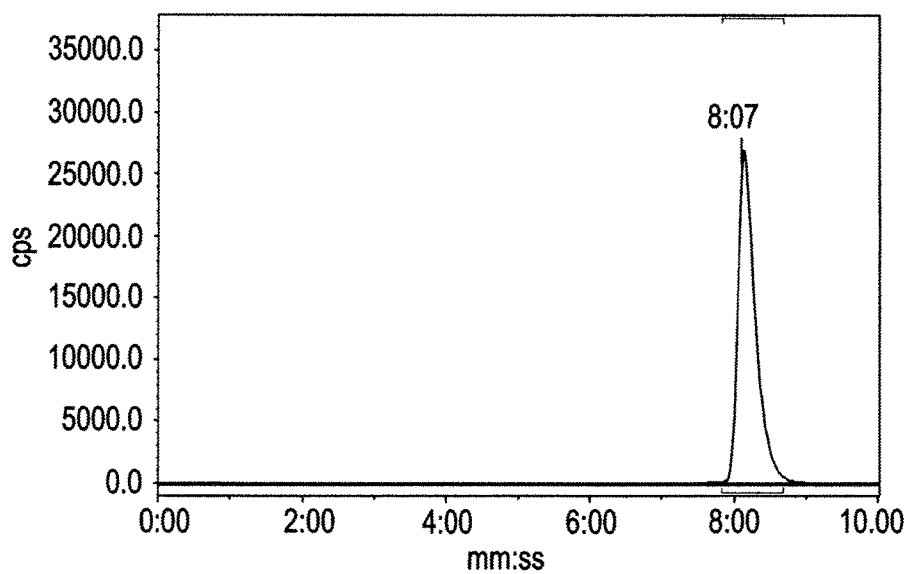
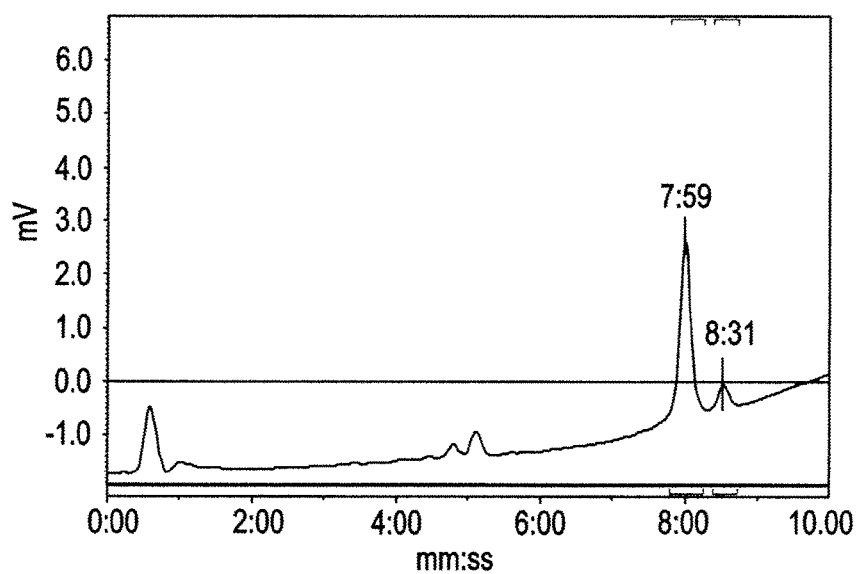

FIG. 6
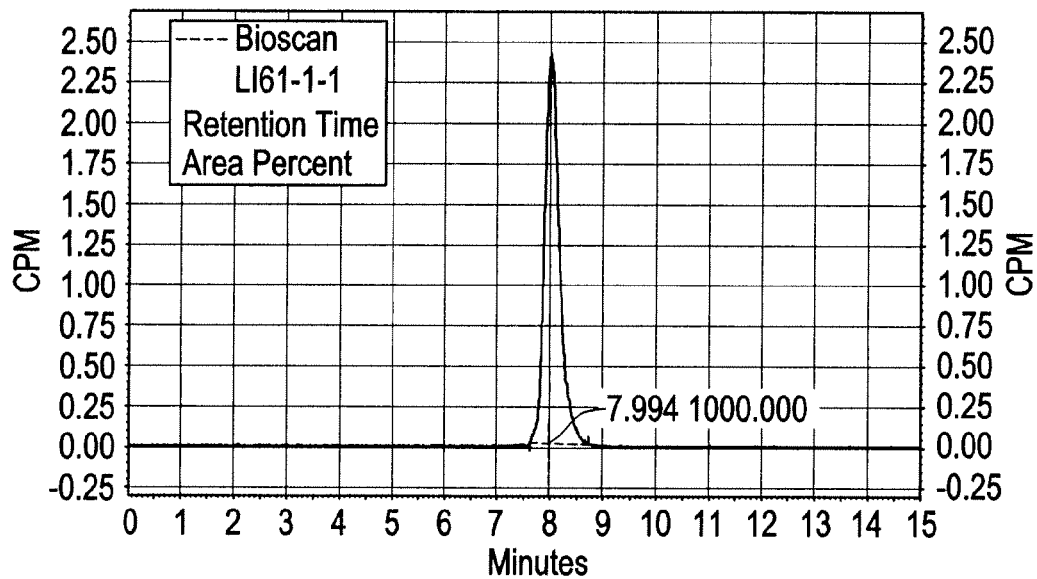
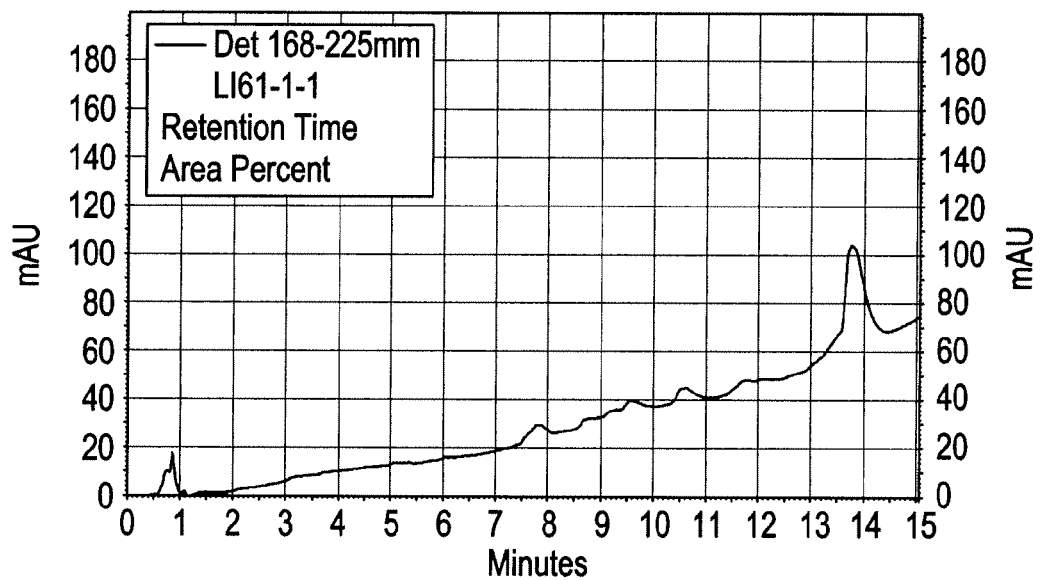

FIG. 7
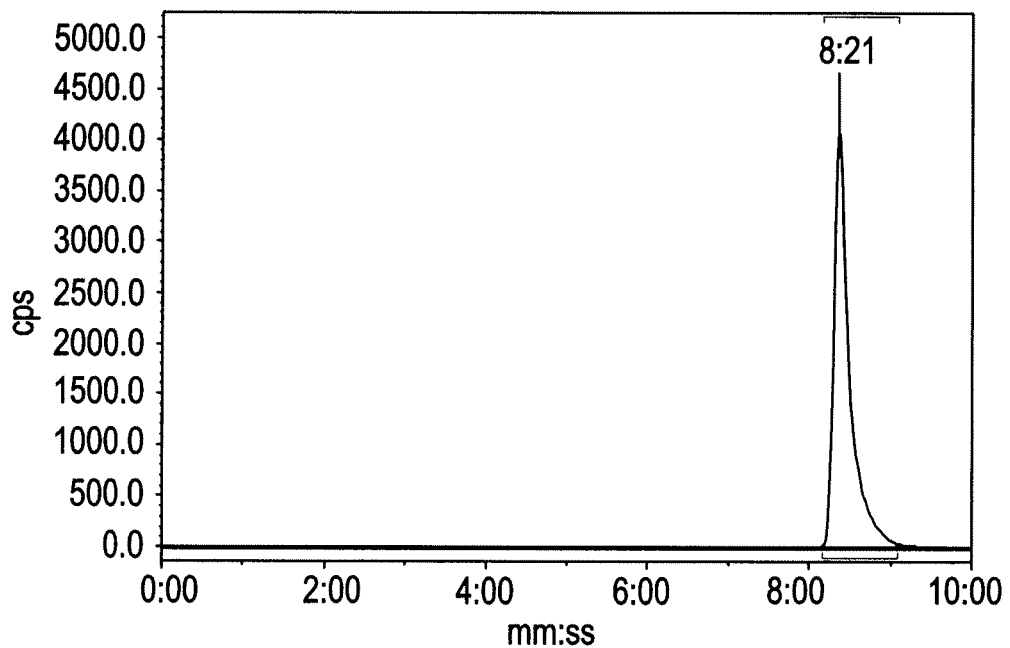
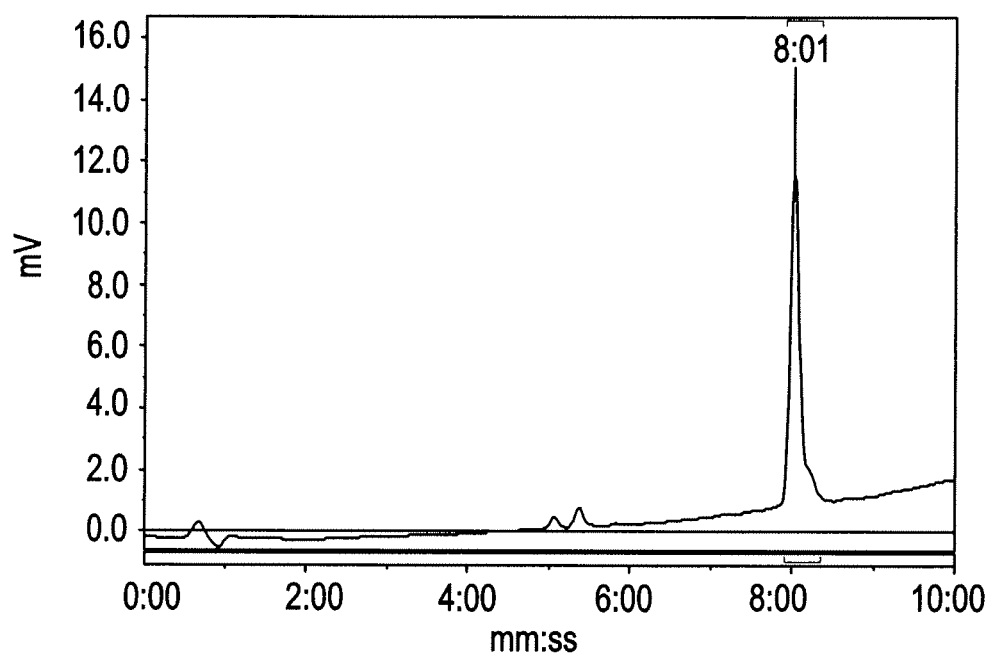

FIG. 8
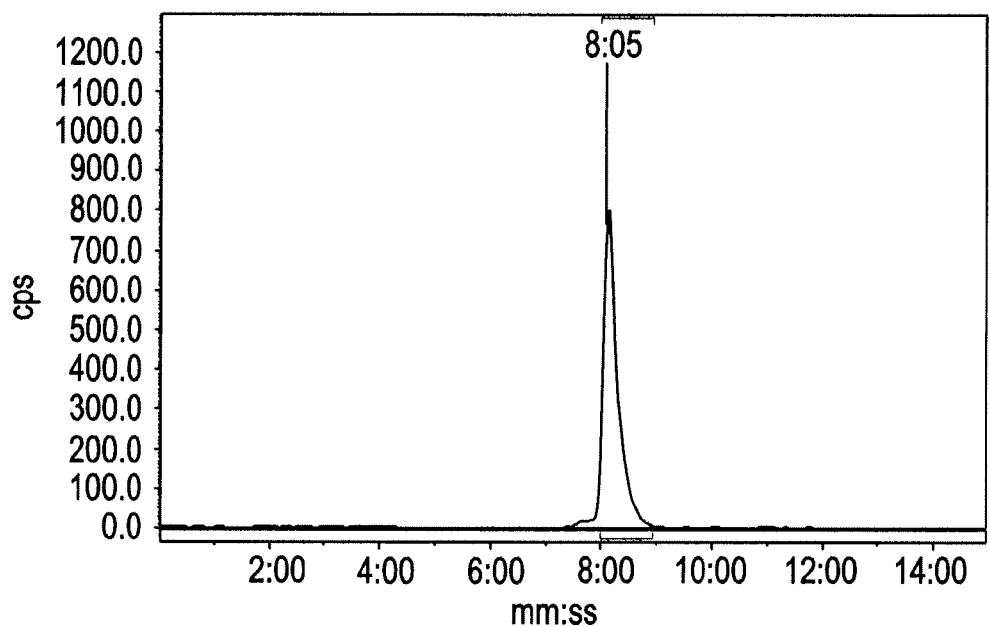
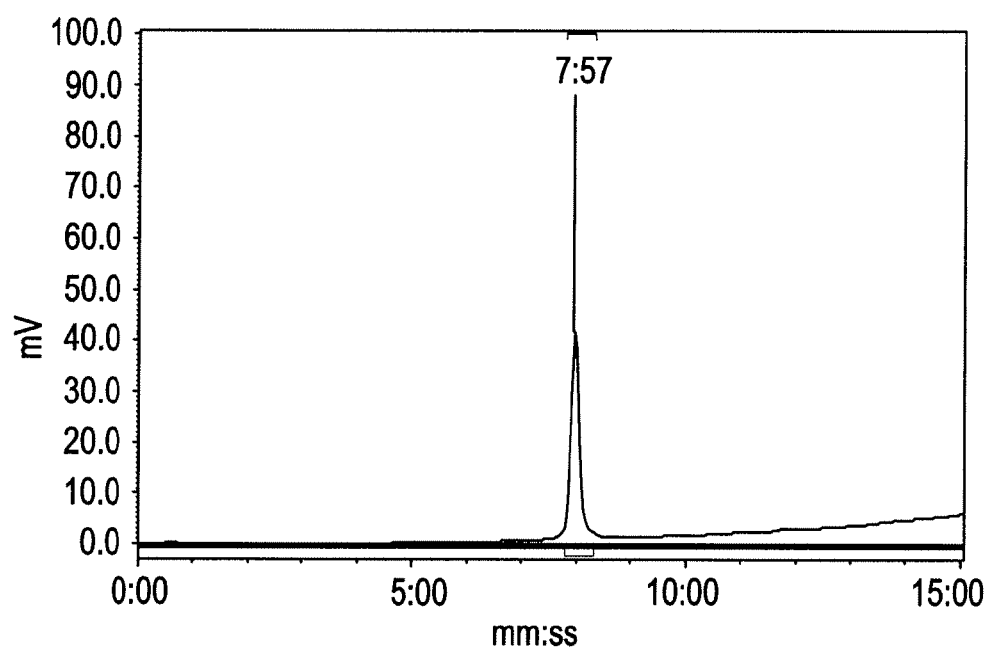

FIG. 9
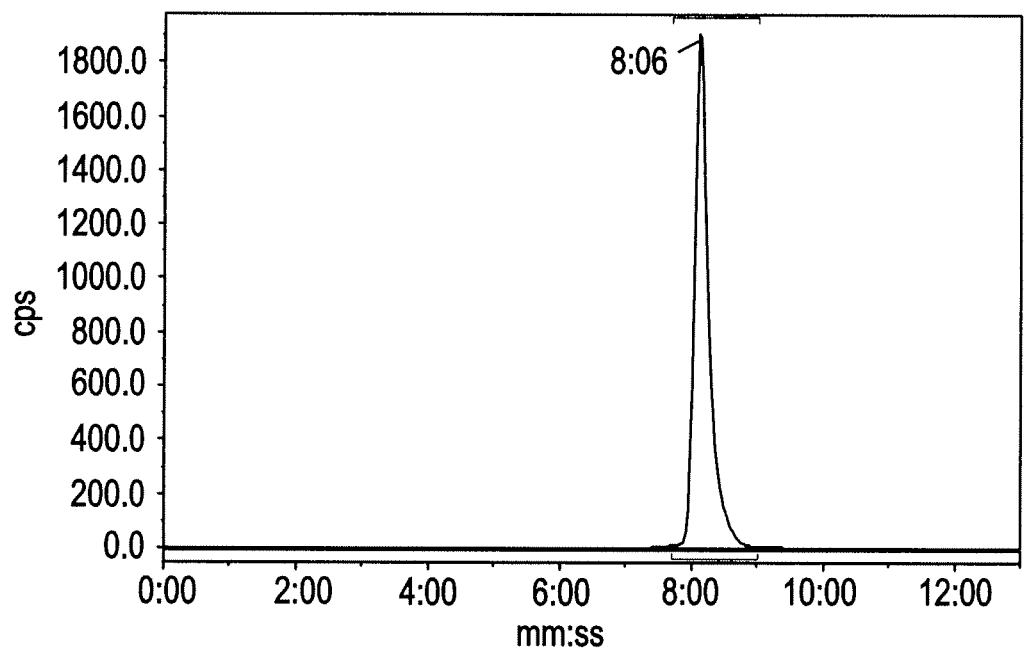
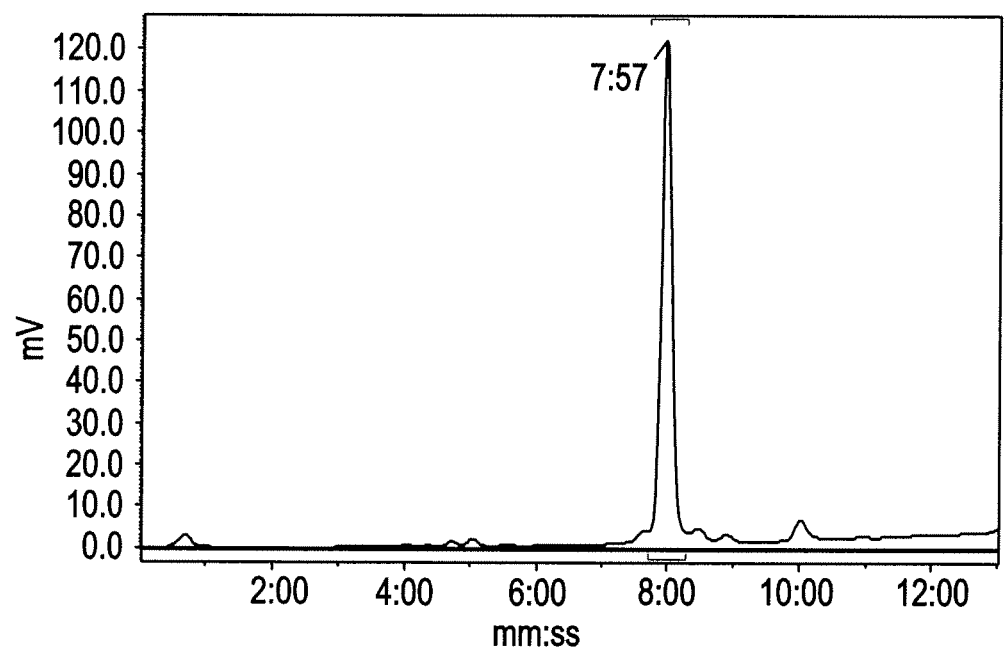

FIG. 10
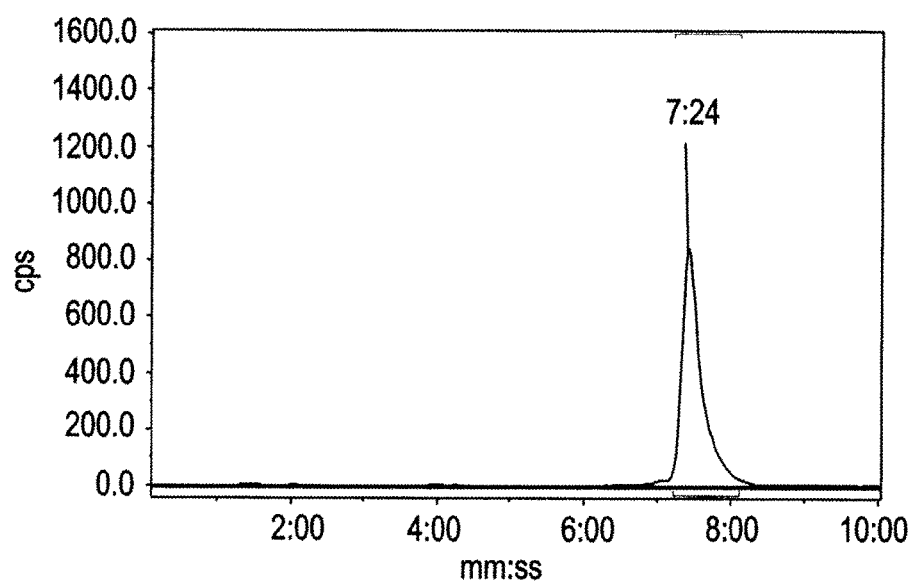
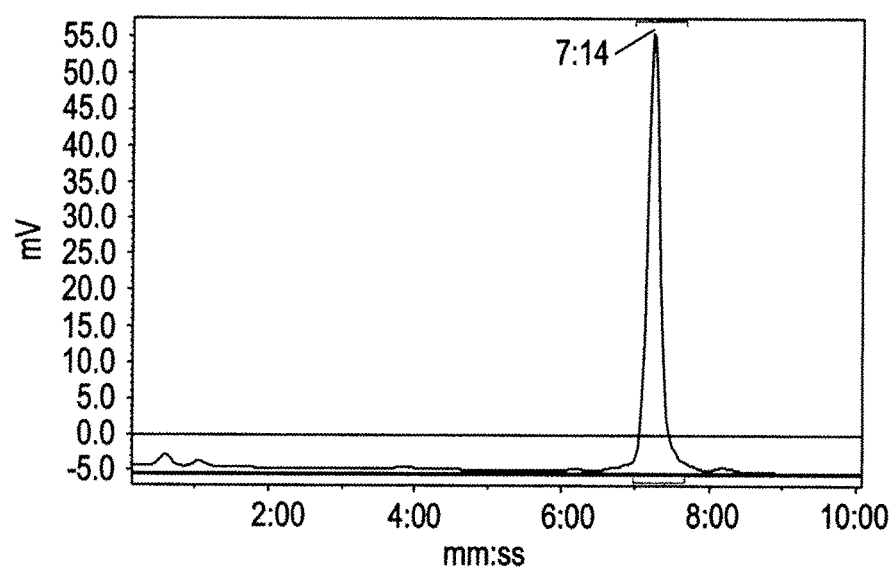

FIG. 11
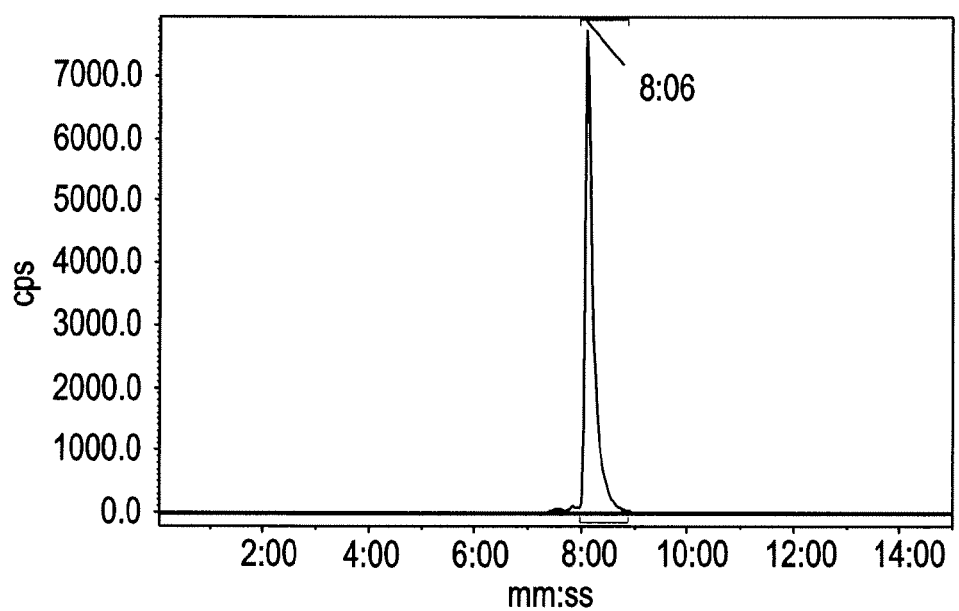
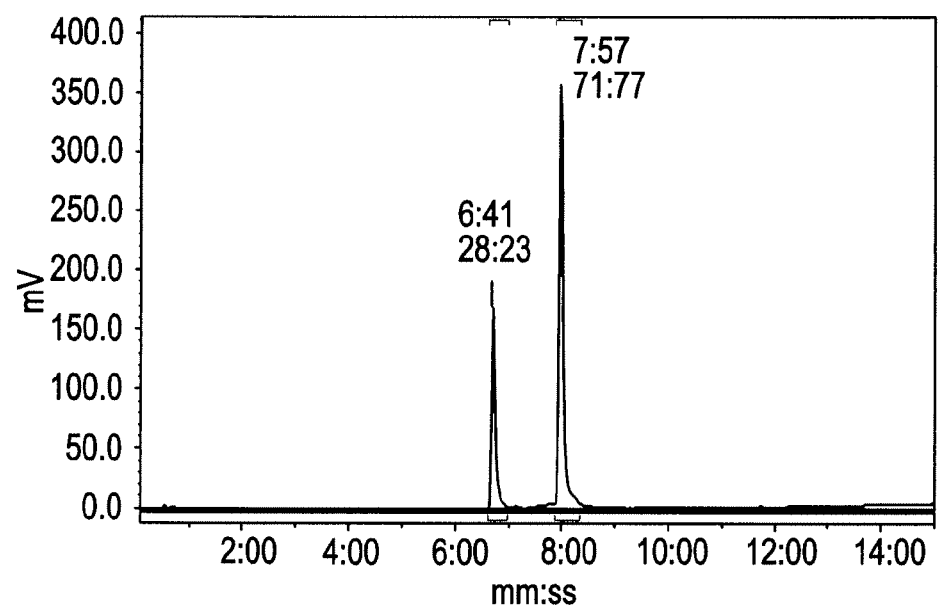

FIG. 12
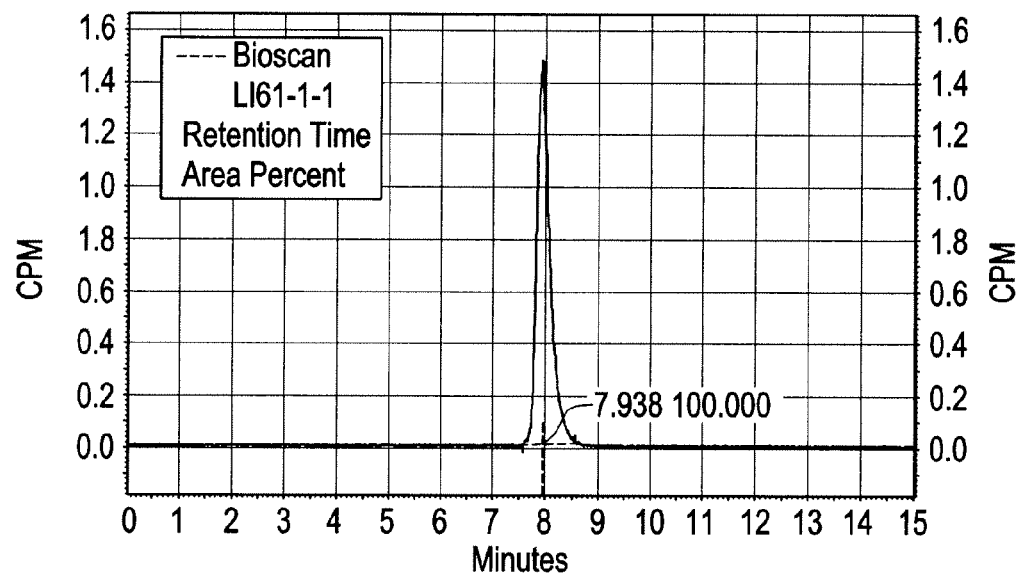
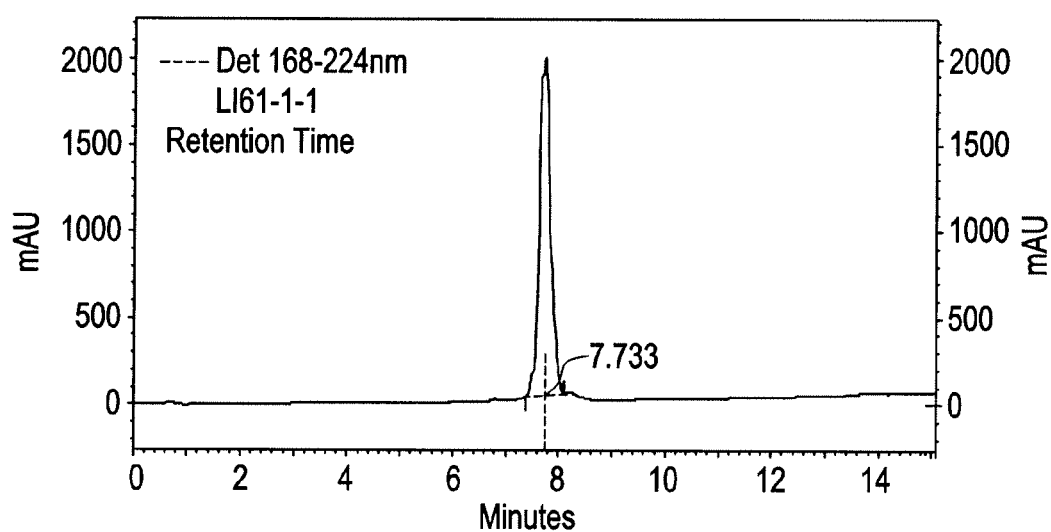

FIG. 13
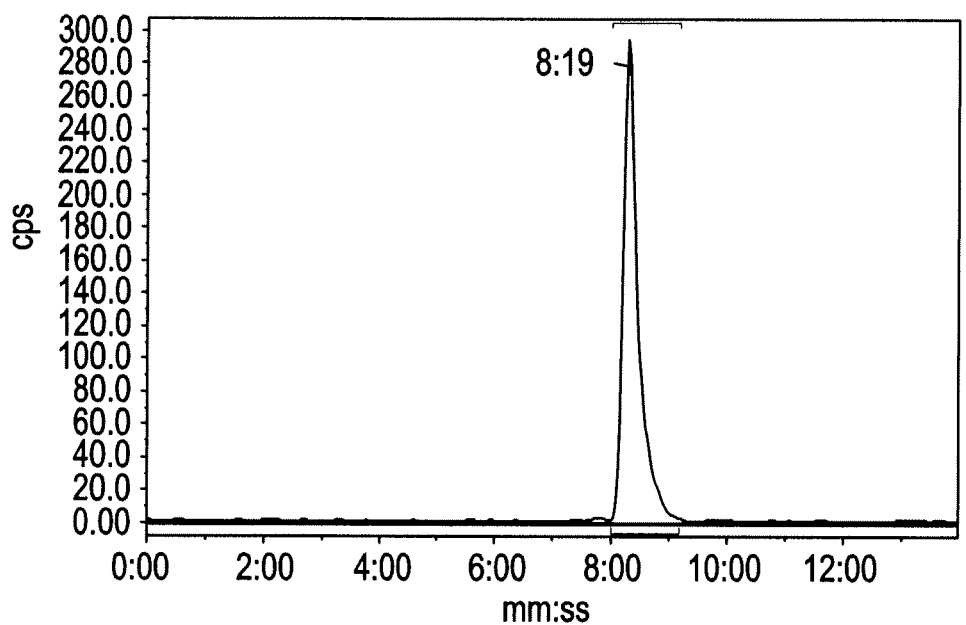
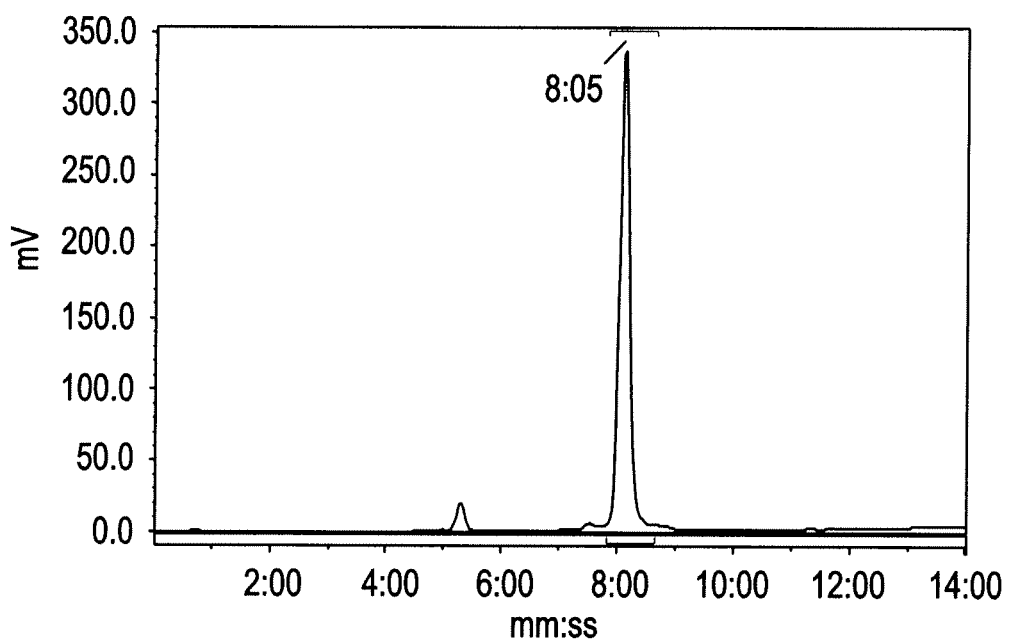

| Compound Identity | Predicted agonist EC$_{50}$ potency value (nM) | | |
|---|---|---|---|
| | sstr-2 | sstr-3 | sstr-4 |
| Somatostatin | 5.6 nM | 9.7 nM | 3.8 nM |
| FET-G-PEG-TOCA | 19.0 nM | ND | >10 mM |
| FETE-PEG-TOCA | 12.0 nM | ND | >10 mM |
| FET-βAG-TOCA | 4.7 nM | ND | 8.6 mM |
| FET-G-TOCA | 6.9 nM | ND | 5.4 mM |
| FETE-TOCA | 4.1 nM | ND | 6.5 mM |
| FET-βAG-[W-c-CTFTYC)K] | 220 nM | ND | ND |

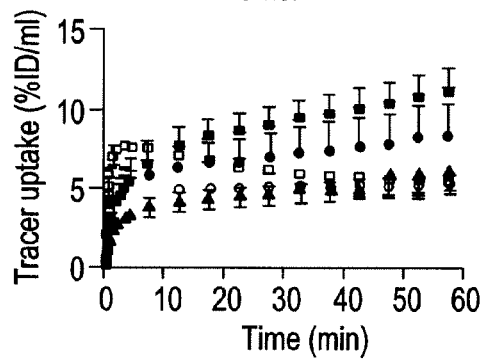
FIG. 17A Tumor
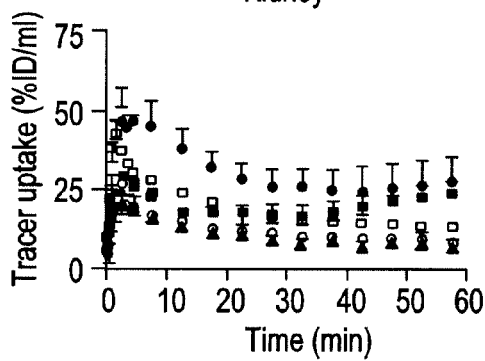
FIG. 17B Kidney
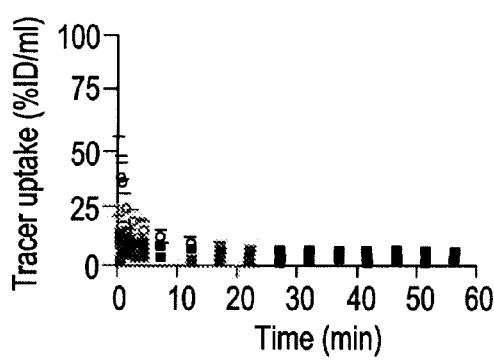
FIG. 17C Liver
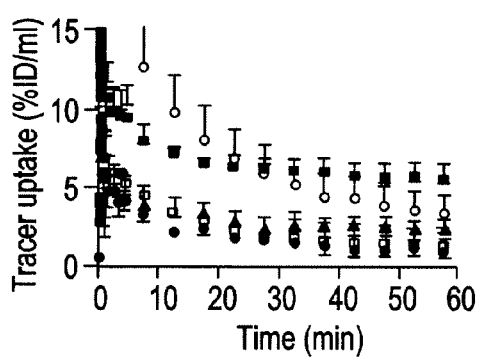
FIG. 17D Liver (zoom)
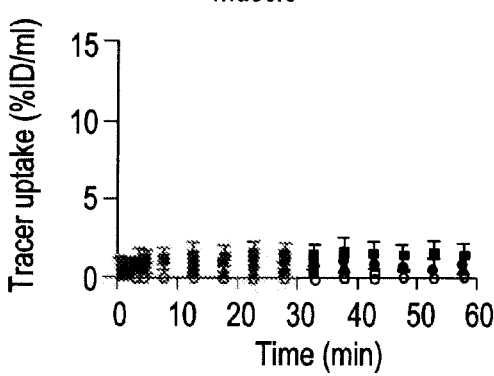
FIG. 17E Muscle
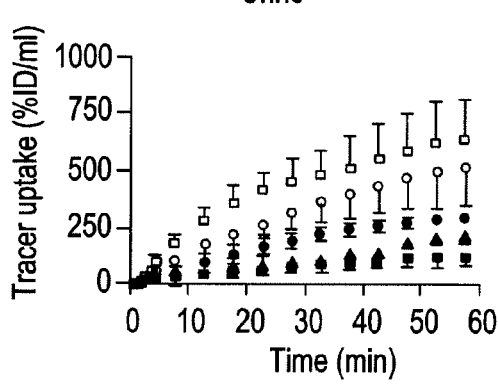
FIG. 17F Urine Tumor Kidney Liver Liver (zoom)

Muscle

Urine

RADIOLABELLED OCTREOTATE ANALOGUES AS PET TRACERS

This application is a filing under 35 U.S.C. 371 of international application number PCT/US2012/207168, filed Mar. 1, 2012, which claims priority to U.S. application No. 61/447,785 filed Mar. 1, 2011, the entire disclosure of each of which is hereby incorporated by reference.

FIELD OF THE INVENTION

The present invention describes a novel radiotracer(s) for Positron Emission Tomography (PET) imaging; specifically imaging of neuroendocrine tumors including gastroenteropancreatic neuorendocrine tumors. Specifically the present invention describes novel [$^{18}$F]Fluoroethyltriazol-[Tyr$^3$]Octreotate analogues. Radiotracers of the present invention can target somatostatin receptors found on the cell surface of gastroenteropancreatic neuroendocrine tumors. The present invention also describes intermediate(s), precursor(s), pharmaceutical composition(s), methods of making, and methods of use of the novel radiotracer(s).

DESCRIPTION OF THE RELATED ART

PET is becoming increasingly important for the early detection of disease in oncology and neurology. Radiolabelled peptides in particular are being investigated more frequently for the detection of disease, the monitoring of treatment, and in peptide receptor radiotherapy (PRRT) (Chen, X. Y., et al., *European Journal of Nuclear Medicine and Molecular Imaging* 2004, 31, (8), 1081-1089; Lei, M., et al., *Current Medical Imaging Reviews* 6, (1), 33-41).

The peptide [Tyr$^3$]octreotate (TOGA) (FIG. 1) has previously been labelled with various radioisotopes for the purpose of imaging (Nikolopoulou, A., et al., *Journal of Peptide Science* 2006, 12, 124-131; Li, W. P., et al., *Bioconjugate Chemistry* 2002, 13, 721-728; Reubi, J. C., et al., *European Journal of Nuclear Medicine and Molecular Imaging* 2000, 27, (3), 273-282) and PRRT of neuroendocrine tumours (Teunissen, J., et al., *European Journal of Nuclear Medicine and Molecular Imaging* 2009, 36, (11), 1758-1766). [Tyr$^3$] Octreotate is a somatostatin analogue that has a longer biological half life (1.5-2 hours) than somatostatin and retains receptor specificity (Weiner, R. E., et al., *Seminars in Nuclear Medicine* 2001, 31, (4), 296-311). It has been found that somatostatin receptors, of which there are 5 subtypes (sstr 1-5), are over expressed on the surface of neuroendocrine tumours (Rufini, V., et al., *Seminars in Nuclear Medicine* 2006, 36, (3), 228-247). This over expression enables selective targeting of tumours with a radiolabelled octreotate analogue. The first discovered eight amino acid sequenced peptide to mimic somatostatin was octreotide. It was found that the cyclic octapeptide contained the important sites for binding to the somatostatin receptor and was initially used as an opiate antagonist (Maurer, R., et al., *PNAS* 1982, 79, 4815-4817) for the treatment of painful conditions such as acute and chronic pancreatitis (Uhl, W., et al., *Digestion, International Journal of Gastroenterology* 1999, 60, 23-31). Comparing octreotide to [Tyr$^3$]octreotate, the latter has been shown to have a higher affinity for the somatostatin receptors (Reubi, J. C., et al., *European Journal of Nuclear Medicine and Molecular Imaging* 2000, 27, (3), 273-282; Wild, R., et al., *European Journal of Nuclear Medicine and Molecular Imaging* 2003, 30, (10), 1338-1347); it appears that substituting phenylalanine for tyrosine and threoninol for threonine at the C-terminus increases affinity. Nonetheless, [$^{111}$In]-DTPA-octreotide (Octreoscan™) is still the peptide of choice in the clinic and was approved by the FDA as an imaging agent for somatostatin receptor positive neuroendocrine tumours in 1994 (Rufini, V., et al., *Seminars in Nuclear Medicine* 2006, 36, (3), 228-247).

Using prosthetic groups (i.e. small radiolabelled organic molecules which can then be coupled to the main pharmacophore of interest) is the strategy generally employed when labelling peptides or other macromolecules to overcome the limitations of $^{18}$F$^-$ such as basicity and poor reactivity (Okarvi, S. M., *European Journal of Nuclear Medicine* 2001, 28, (7), 929-38). The approaches used to date all vary in the number of steps involved, the overall reaction time, isolated yield and method of isolation. Octreotide has previously been labelled with $^{18}$F-modified organic prosthetic groups. The initial strategy employed by Hostetler et al. (*Journal of Labelled Compounds & Radiopharmaceuticals* 1999, 42, S720-S721) was to directly label the N-terminus of octreotide with the activated ester of [$^{18}$F]fluorobenzoic acid ([$^{18}$F]FBA). Subsequent biodistribution studies showed that the [$^{18}$F]fluorobenzoyl-octreotide analogue was too lipophilic and showed significant uptake in the liver. Octreotide has also been directly labelled at the N-terminus with 2-[$^{18}$F]fluoropropionate 4-nitrophenylester, which itself involves three chemical modification steps to synthesize (Guhlke, S., et al., *Applied Radiation and Isotopes* 1994, 45, (6), 715-727). The main drawback to this chemistry is the need to Boc-protect the lysine side chain of octreotide during conjugation which requires removal in the final step (Guhlke, S., et al., *Nuclear Medicine and Biology* 1994, 21, (6), 819-825).

Schottelius et al. (*Clinical Cancer Research* 2004, 10, (11), 3593-3606) wanted to develop an $^{18}$F-labelled octreotate analogue with improved tumour uptake and better pharmacokinetics compared to previous analogues. The authors chose to modify octreotate with carbohydrate groups in order to reduce lipophilicity, to consequently reduce hepatic elimination and conversely aid renal elimination. A glucose modified octreotate (Gluc-Lys-TOCA) was developed and the lysine of the peptide labelled with 2-[$^{18}$F] fluoropropionate 4-nitrophenylester. The final product Gluc-Lys([$^{18}$F]FP)-TOCA was evaluated in patients by Meisetschlager et al. (*Journal of Nuclear Medicine* 2006, 47, 566-573) and was found to be superior to [$^{111}$In]-DTPA-octreotide at detection of neuroendocrine tumours. However while [$^{111}$In]-DTPA-octreotide showed improvements in tumour uptake, the lengthy synthesis time (3 hours) and low yields (20-30%) made it a non-viable option for routine clinical use (Meisetschläger, G., et al., *Journal of Nuclear Medicine* 2006, 47, 566-573). Schottelius et al. (*Clinical Cancer Research* 2004, 10, (11), 3593-3606) also labelled two other carbohydrate analogues, Cel-S-Dpr-[Tyr$^3$]octreotate and Gluc-S-Dpr[Tyr$^3$]octreotate with [$^{18}$F]fluorobenzaldehyde to give the oxime-derivatised radiotracers. The Cel-S-Dpr([$^{18}$F]FBOA)-[Tyr$^3$]octreotate showed improved tumour uptake compared to Gluc-Lys([$^{18}$F]FP)-TOCA and had a shorter synthesis time (50 min) with improved yields (65-85%). Gluc-S-Dpr[Tyr$^3$]octreotate was labelled with both [$^{18}$F]-fluoropropionate ([$^{18}$F]FP) and [$^{18}$F]fluorobenzaldehyde ([$^{18}$F]FBOA). The Gluc-S-Dpr-([$^{18}$F]FP)-Tyr$^3$]octreotate labelled analogue showed tumor uptake similar to Gluc-Lys([$^{18}$F]FP)-TOCA but also had high tumour to organ ratios (blood, liver and muscle). The Gluc-S-Dpr-([$^{18}$F] FBOA)[Tyr$^3$]octreotate showed comparable tumour uptake to Cel-S-Dpr([$^{18}$F]FBOA)-[Tyr$^3$]octreotate, but had a high tumour/muscle ratio.

The most recently published $^{18}$F-labelled octreotide analogue was [$^{18}$F]-aluminum fluoride—1,4,7-triazacyclononane-1,4,7-triacetic acid octreotide ([$^{18}$F]AlF-NOTA-Octreotide) (Layerman, P., et al., *Journal of Nuclear Medicine* 51, (3), 454-461). The advantage of using the [$^{18}$F]aluminium fluoride labelling strategy is that the fluorine-18 azeotropic drying step is not required, meaning shorter overall reaction times. By HPLC, the product was observed as two isomers, equating to approximately 50% incorporation of [$^{18}$F]AlF into the NOTA chelate, the remainder was stated as non-chelated [$^{18}$F]AlF. The authors commented that the two isomers could be separated by HPLC. When re-analysed they saw re-equilibration to the two isomers. The conformation of these two isomers has not been established to date.

Click chemistry has been utilised previously in fluorine-18 labelling of peptides (Li, Z. B., et al., *Bioconjugate Chemistry* 2007, (18), 1987-1994; Ramenda, T., et al., *Chemical Communications* 2009, 48, 7521-7523; Hausner et al. *J. Med. Chem.*, 2008, 5901; Mamat et al. *Mini-Rev. Org. Chem.* 2009, 6, 21). Since the reaction is efficient it can be applied to the synthesis of radiolabelled tracers and ligands with short lived isotopes (half life $^{18}$F, 109.7 min) for positron emission tomography (PET)(Glaser, M., and Arstad, E., *Bioconjugate Chemistry* 2007, 18, (3), 989-993; Glaser, M., et al., *Journal of Labelled Compounds & Radiopharmaceuticals* 2009, 52, (9-10), 407-414).

Marik and Sutcliffe (Marik, J., et al., *Tetrahedron Letters* 2006, (47), 6681-6684) took the approach of labelling terminal alkynes with fluorine-18 and adding the azide moiety to various peptides. CuSO$_4$/Na-ascorbate was initially employed as a catalytic system but the labelled peptide was only isolated in 10% yield. Improvements were observed when CuSO$_4$ was replaced by CuI with addition of N,N-diisopropylethylamine (DIPEA). Sirion et al. (*Tetrahedron Letters* 2007, 48, 3953-3957) found that using CuI gave traces of the 1,5-substituted triazole by-product. The authors synthesized four mesylate precursors, two acetylene and two azides all of which were labelled using [$^{18}$F]TBAF, with tBuOH as solvent (Kim, D. W., et al., *Journal of the American Chemical Society* 2006, 128, 16394-16397).

However there still exists a need in the art for radiolabeled octreotate analogues with improved tumour uptake and pharmacokinetic parameters compared to previously labelled analogues. There also exists a need for an efficient and effective method to prepare such radiolabeled octreotate analogues. The present invention, as described below, answers these needs.

BRIEF DESCRIPTION OF THE DRAWINGS

FIG. 2 depicts HPLC Analysis of FET-G-PEG-TOGA (1b) carried out using a Phenomenex Luna C18(2) column (50×4.6 mm, 3 µm; flow rate 1 mL/min) using a gradient of 5-80% ACN/0.1% TFA over 15 min.

FIG. 4 depicts HPLC Analysis of FET-G-TOCA (3b) carried out using a Phenomenex Luna C18(2) column (50×4.6 mm, 3 µm; flow rate 1 mL/min) using a gradient of 5-80% ACN/0.1% TFA over 15 min.

FIG. 5 depicts HPLC Analysis of FETE-TOGA (4b) carried out using a Phenomenex Luna C18(2) column (50×4.6 mm, 3 µm; flow rate 1 mL/min) using a gradient of 5-80% ACN/0.1% TFA over 15 min.

FIG. 6 depicts HPLC Analysis of FET-βAG-TOGA (5b) carried out using a Phenomenex Luna C18(2) column (50×4.6 mm, 3 µm; flow rate 1 mL/min) using a gradient of 5-80% ACN/0.1% TFA over 15 min.

FIG. 7 depicts HPLC Analysis of FET-βAG-[W-c(CT-FTYC)K] (6b) carried out using a Phenomenex Luna C18(2) column (50×4.6 mm, 3 µm; flow rate 1 mL/min) using a gradient of 5-80% ACN/0.1% TFA over 15 min.

FIG. 8 depicts HPLC Analysis of FET-G-PEG-TOGA (1b) spiked with [$^{19}$F]-standards carried out using a Phenomenex Luna C18(2) column (50×4.6 mm, 3 µm; flow rate 1 mL/min) using a gradient of 5-80% ACN/0.1% TFA over 15 min.

FIG. 9 depicts HPLC Analysis of FETE-PEG-TOGA (2b) spiked with [$^{19}$F]-standards carried out using a Phenomenex Luna C18(2) column (50×4.6 mm, 3 µm; flow rate 1 mL/min) using a gradient of 5-80% ACN/0.1% TFA over 15 min.

FIG. 10 depicts HPLC Analysis of FET-G-TOCA (3b) spiked with [$^{19}$F]-standards carried out using a Phenomenex Luna C18(2) column (50×4.6 mm, 3 µm; flow rate 1 mL/min) using a gradient of 5-80% ACN/0.1% TFA over 15 min.

FIG. 11 depicts HPLC Analysis of FETE-TOCA (4b) spiked with [$^{19}$F]-standards carried out using a Phenomenex Luna C18(2) column (50×4.6 mm, 3 µm; flow rate 1 mL/min) using a gradient of 5-80% ACN/0.1% TFA over 15 min. This analogue appears to show signs of degradation overtime, due to being stored in aqueous solution for >1 month; hence the two peaks. On initial formation the [$^{19}$F] FETE-TOCA was seen as one peak only.

FIG. 12 depicts HPLC Analysis of FET-βAG-TOCA (5b) spiked with [$^{19}$F]-standards carried out using a Phenomenex Luna C18(2) column (50×4.6 mm, 3 µm; flow rate 1 mL/min) using a gradient of 5-80% ACN/0.1% TFA over 15 min.

FIG. 13 depicts HPLC Analysis of FET-βAG-[W-c(CT-FTYC)K] (6b) spiked with [$^{19}$F]-standards carried out using a Phenomenex Luna C18(2) column (50×4.6 mm, 3 µm; flow rate 1 mL/min) using a gradient of 5-80% ACN/0.1% TFA over 15 min.

FIG. 17. Time activity curves comparing the tissue pharmacokinetics of [$^{18}$F]ethyltriazole-[Tyr$^3$]octreotate analogs in AR42J tumor, kidney, liver, muscle, and urine. Dynamic PET/CT imaging was performed for 60 min after i.v. injection of each radiotracer into tumor bearing mice. For clarity, the liver curves have been expanded (zoom). Tissue radiotracer uptake values are expressed as % injected dose/mL of tissue. Values represent the mean±SEM (n=3-5); upper and lower bars are used for clarity. Symbols are (□) FET-G-PEG-TOCA, (○) FETE-PEG-TOGA, (•) FET-βAG-TOCA, (■) FET-G-TOCA, and (▲) FETE-TOGA.

SUMMARY OF THE INVENTION

Figure 1:
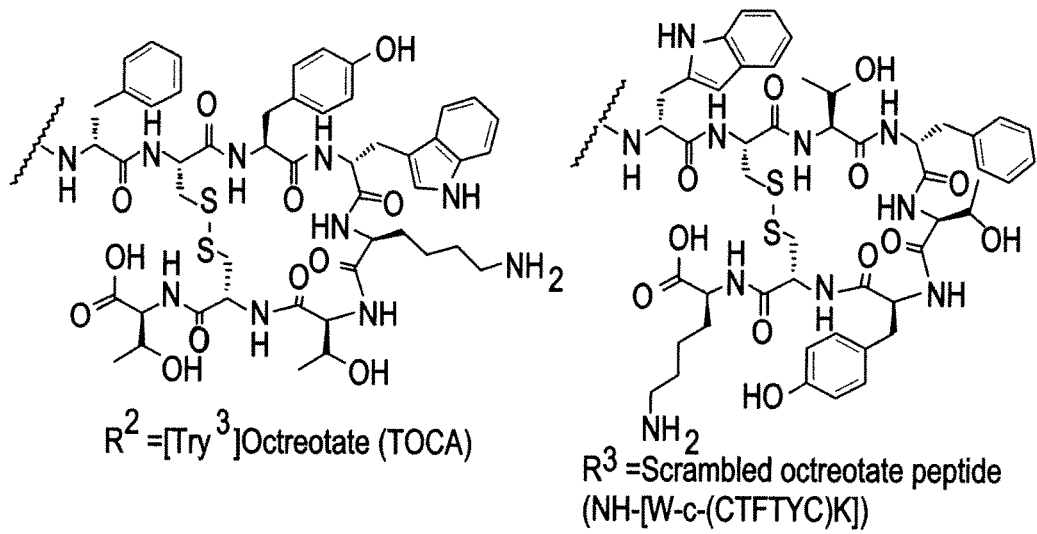
FIG. 1 describes the peptide [Tyr$^3$]octreotate (TOGA), five alkyne (1a-5a) and triazole (1b-5b) octreotate analogues, and the scrambled negative control alkyne (6a) and triazole (6b).

The present invention provides a triazole linked [Tyr$^3$] octreotate analogue(s).

The present invention provides a 2-[$^{18}$F]fluoroethyl triazole linked [Tyr$^3$]Octreotate analogue(s). A compound of the present invention combines high specific binding with rapid target localization and rapid pharmacokinetics for high contrast PET imaging.

The present invention provides a method of making a 2-[$^{18}$F]fluoroethyl triazole linked [Tyr$^3$]Octreotate analogue(s) of the invention.

The present invention provides a method of imaging using a 2-[$^{18}$F]fluoroethyl triazole linked [Tyr$^3$]Octreotate analogue(s) of the invention.

The present invention provides an alkyne linked [Tyr$^3$] Octreotate analogue(s) and a method of making the same.

The present invention provides a pharmaceutical composition comprising at least one 2-[$^{18}$F]fluoroethyl triazole linked [Tyr$^3$]Octreotate analogue of the invention together with a pharmaceutically acceptable carrier, excipient, or biocompatible carrier.

The present invention further provides a method of detecting somatostatin receptor in vitro or in vivo comprising administering a 2-[$^{18}$F]fluoroethyl triazole linked [Tyr$^3$] Octreotate analogue(s) of the invention or a pharmaceutical composition thereof.

The present invention further provides a method of detecting somatostatin receptor in vitro or in vivo using a 2-[$^{18}$F] fluoroethyl triazole linked [Tyr$^3$]Octreotate analogue(s) of the invention or a pharmaceutical composition thereof.

DETAILED DESCRIPTION OF THE INVENTION

The present invention provides a triazole linked [Tyr$^3$] octreotate analogue of Formula (I):

R$_1$-LINKER-R$_2$  (I)

wherein:
R$_1$ is

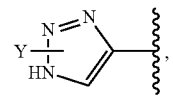

wherein Y is a reporter moiety that contains at least one radioisotope;
R$_2$ has the following structure:

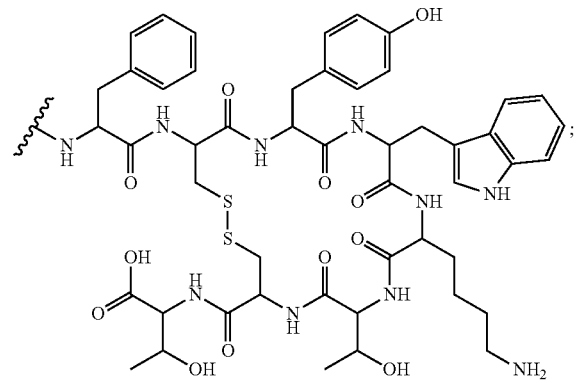 [SMILES: *NC(Cc1ccccc1)C(=O)NC1CSSCC(C(=O)NC(C(=O)O)C(C)O)NC(=O)C(C(C)O)NC(=O)C(CCCCN)NC(=O)C(Cc2c[nH]c3ccccc23)NC(=O)C(Cc2ccc(O)cc2)NC1=O]

and
LINKER is a linker group as described in WO2008139207 or a synthetic linker group of formula -(A)$_m$- wherein each A is independently —CR$_2$—, —CR=CR—

—CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a C$_{4-8}$cycloheteroalkylene group, a C$_{4-8}$cycloalkylene group, a C$_{5-12}$arylene group, or a C$_{3-12}$heteroarylene group, an amino acid, a sugar or a monodisperse polyethyleneglycol (PEG) building block; each R is independently chosen from H, C$_{1-20}$alkyl, C$_{2-4}$alkenyl, C$_{2-4}$alkynyl, C$_{1-4}$alkoxy C$_{1-20}$alkyl or hydroxy C$_{1-20}$alkyl; m is an integer of value 1 to 20.

According to the invention, the radioisotope of the reporter moiety Y can be any radioisotope known in the art. In one embodiment, the radioisotope is any PET radioisotope known in the art (e.g., $^{18}$F, $^{17}$Br, $^{76}$Br, $^{124}$I, $^{11}$C, $^{82}$Rb, $^{68}$Ga, $^{64}$Cu and $^{62}$Cu; preferably, $^{11}$C or $^{18}$F; most preferably, $^{18}$F). In one embodiment, the radioisotope is any SPECT radioisotope known in the art (e.g., $^{123}$I, $^{124}$I, $^{131}$I). The radioisotope may be directly incorporated into the reporter moiety Y (e.g. —CH$_2$CH$_2$$^{18}$F or —CH$_2$CH$_2$$^{11}$CH$_2$F) or may be incorporated into a chelating agent by methods known in the art (see e.g. WO 2006/067376).

The present invention provides a 2-fluoroethyl triazole linked [Tyr$^3$]octreotate analogue of Formula (II):

R$_1$-LINKER-R$_2$     (II)

wherein:
R$_1$ is

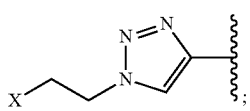

wherein X is a radioisotope as described above and wherein LINKER and R$_2$ are each as described for Formula (I).

The present invention provides a 2-[$^{18}$F]fluoroethyl triazole linked [Tyr$^3$]octreotate analogue of Formula (III):

R$_1$-LINKER-R$_2$     (III)

wherein:

R$_1$ is 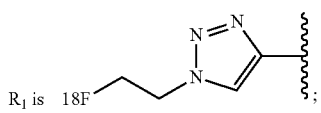

R$_2$ has the following structure:

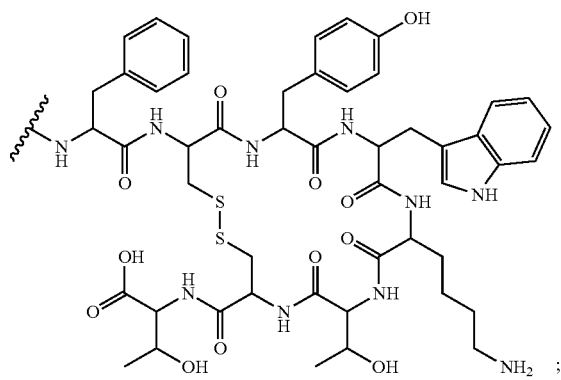 [SMILES: *NC(Cc1ccccc1)C(=O)NC1CSSCC(C(=O)NC(C(=O)O)C(C)O)NC(=O)C(C(C)O)NC(=O)C(CCCCN)NC(=O)C(Cc2c[nH]c3ccccc23)NC(=O)C(Cc2ccc(O)cc2)NC1=O ; ";"]

and

LINKER is a linker group as described in WO2008139207 or a synthetic linker group of formula -(A)$_m$- wherein each A is independently —CR$_r$—, —CR═CR—,

—C≡C—,

—CR$_2$CO$_2$—, —CO$_2$CR$_2$—, —NRCO—, —CONR—, —NR(C═O)NR—, —NR(C═S)NR—, —SO$_2$NR—, —NRSO$_2$—, —CR$_2$OCR$_2$—, —CR$_2$SCR$_2$—, —CR$_2$NRCR$_2$—, a C$_{4-8}$cycloheteroalkylene group, a C$_{4-8}$cycloalkylene group, a C$_{5-12}$arylene group, or a C$_{3-12}$heteroarylene group, an amino acid, a sugar or a monodisperse polyethyleneglycol (PEG) building block; each R is independently chosen from H, C$_{1-20}$alkyl, C$_{2-4}$alkenyl, C$_{2-4}$alkynyl, C$_{1-4}$alkoxy C$_{1-20}$alkyl or hydroxy C$_{1-20}$alkyl; m is an integer of value 1 to 20.

The present invention provides a triazole linked [Tyr$^3$] octreotate analogue of Formulae (I), (II) and/or (III), each as described above, wherein R$_1$ and R$_2$ are each as described above for Formulae (I), (II) and (III) and LINKER is
-(polyethylene glycol)$_n$-;

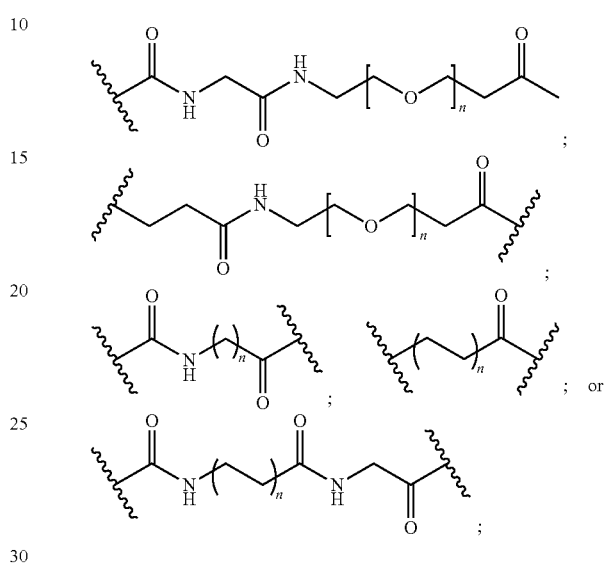

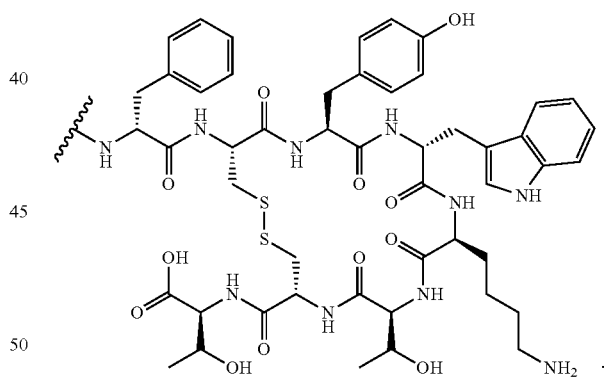

wherein n is an integer from 1-20; preferably, n is an integer from 1-10; more preferably, n is an integer from 1-6.

In one embodiment of the invention, R$_2$ compound of Formulae (I), (II) and (III) each as described above is:

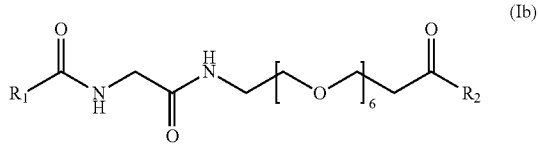

The present invention provides 2-[$^{18}$F]fluoroethyl triazole linked [Tyr$^3$]octreotate analogue, FET-G-PEG-TOCA, of Formula (Ib):

(Ib)

wherein:

R₁ is

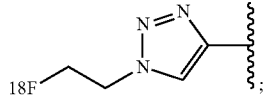

and

R₂ has the following structure:

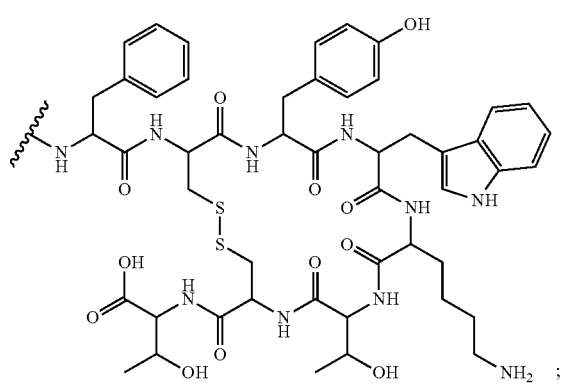 [SMILES: *NC(Cc1ccccc1)C(=O)NC1CSSCC(C(=O)NC(C(=O)O)C(C)O)NC(=O)C(C(C)O)NC(=O)C(CCCCN)NC(=O)C(Cc2c[nH]c3ccccc23)NC(=O)C(Cc2ccc(O)cc2)NC1=O ; ";"]

preferably, R₂ has the following structure:

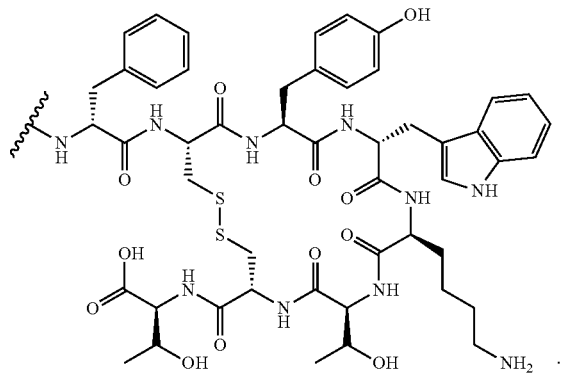 [SMILES: *N[C@H](Cc1ccccc1)C(=O)N[C@H]1CSSC[C@@H](C(=O)N[C@H](C(=O)O)C(C)O)NC(=O)[C@H](C(C)O)NC(=O)[C@H](CCCCN)NC(=O)[C@@H](Cc2c[nH]c3ccccc23)NC(=O)[C@H](Cc2ccc(O)cc2)NC1=O ; "."]

The present invention provides 2-[$^{18}$F]fluoroethyl triazole linked [Tyr³]octreotate analogue, FETE-PEG-TOGA, of Formula (2b):

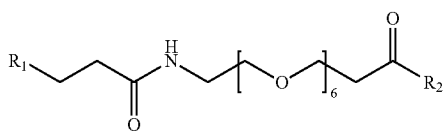

wherein R₁ and R₂ are each as described above for the compound of Formula (Ib).

The present invention provides 2-[$^{18}$F]fluoroethyl triazole linked [Tyr³]octreotate analogue, FET-G-TOGA (3b):

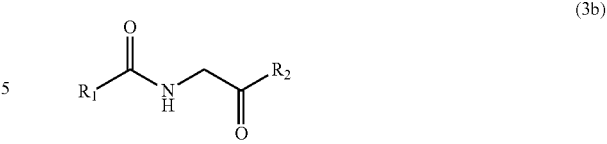

wherein R₁ and R₂ are each as described above for the compound of Formula (Ib).

The present invention provides 2-[$^{18}$F]fluoroethyl triazole linked [Tyr³]octreotate analogue, FETE-TOGA (4b):

wherein R₁ and R₂ are each as described above for the compound of Formula (Ib).

The present invention provides 2-[$^{18}$F]fluoroethyl triazole linked [Tyr³]octreotate analogue, FET-βAG-TOGA (5b):

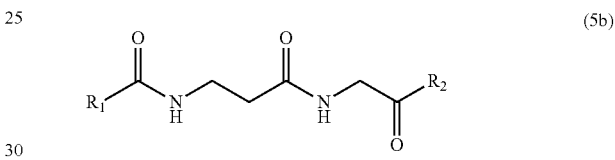

wherein R₁ and R₂ are each as described above for the compound of Formula (Ib).

The present invention provides 2-[$^{18}$F]fluoroethyl triazole linked [Tyr³]octreotate analogue, FET-βAG-[W-c-(CT-FTYC)K] (7b):

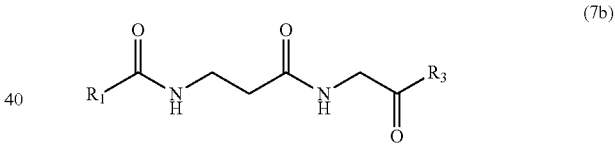

wherein R₁ is as described above for the compound of Formula (Ib) and R₃ is:

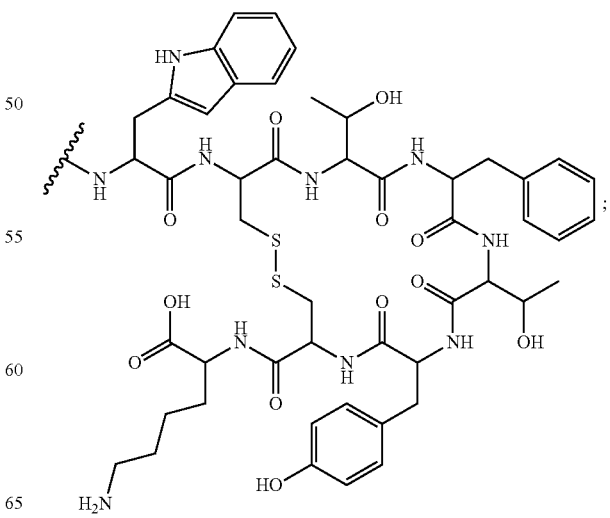

preferably, $R_3$ has the following structure:

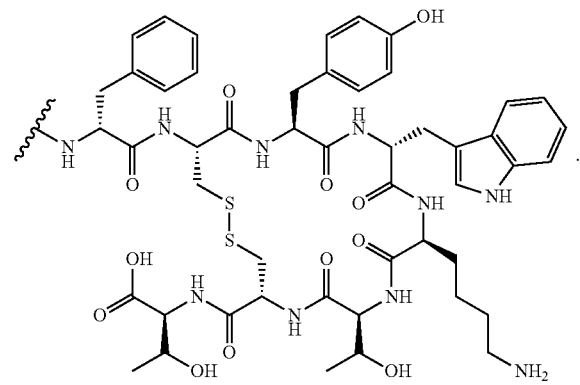 [SMILES: *N[C@H](Cc1ccccc1)C(=O)N[C@H]1CSSC[C@@H](C(=O)N[C@H](C(=O)O)C(C)O)NC(=O)[C@H](C(C)O)NC(=O)[C@H](CCCCN)NC(=O)[C@@H](Cc2c[nH]c3ccccc23)NC(=O)[C@H](Cc2ccc(O)cc2)NC1=O]

Pharmaceutical or Radiopharmaceutical Composition

The present invention provides a pharmaceutical composition comprising at least one triazole linked [Tyr$^3$]octreotate analogue or 2-[$^{18}$F]fluoroethyl triazole linked [Tyr$^3$]octreotate analogue of the invention, as described herein, together with a pharmaceutically acceptable carrier, excipient, or biocompatible carrier.

The present invention provides a pharmaceutical composition comprising at least one triazole linked [Tyr$^3$]octreotate analogue or 2-[$^{18}$F]fluoroethyl triazole linked [Tyr$^3$]octreotate analogue of the invention, as described herein, together with a pharmaceutically acceptable carrier, excipient, or biocompatible carrier suitable for mammalian administration.

As would be understood by one of skill in the art, the pharmaceutically acceptable carrier, excipient, or biocompatible carrier can be any pharmaceutically acceptable carrier, excipient, or biocompatible carrier known in the art.

The "pharmaceutically acceptable carrier, excipient, or biocompatible carrier" can be any fluid, especially a liquid, in which a triazole linked [Tyr$^3$]octreotate analogue or a 2-[$^{18}$F]-fluoroethyl triazole linked [Tyr$^3$]octreotate analogue of the invention can be suspended or dissolved, such that the pharmaceutical composition is physiologically tolerable, e.g., can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g., salts of plasma cations with biocompatible counterions), sugars (e.g., glucose or sucrose), sugar alcohols (e.g., sorbitol or mannitol), glycols (e.g., glycerol), or other non-ionic polyol materials (e.g., polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

A pharmaceutical composition of the invention may be administered parenterally, i.e., by injection, and is most preferably an aqueous solution. Such a composition may optionally contain further ingredients such as buffers; pharmaceutically acceptable solubilisers (e.g., cyclodextrins or surfactants such as Pluronic, Tween or phospholipids); pharmaceutically acceptable stabilisers or antioxidants (such as ascorbic acid, gentisic acid or para-aminobenzoic acid). A method for preparation of a pharmaceutical composition of the invention may further comprise the steps required to obtain a pharmaceutical composition comprising a radiolabeled compound, e.g., removal of organic solvent, addition of a biocompatible buffer and any optional further ingredients. For parenteral administration, steps to ensure that the pharmaceutical composition of the invention is sterile and apyrogenic also need to be taken. Such steps are well-known to those of skill in the art.

INTERMEDIATES

The present invention provides an alkyne linked [Tyr$^3$] octreotate analogue of Formula (IV):

$$R_1\text{-LINKER-}R_2 \qquad (IV)$$

wherein:

$R_1$ is

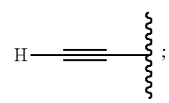

$R_2$ has the following structure:

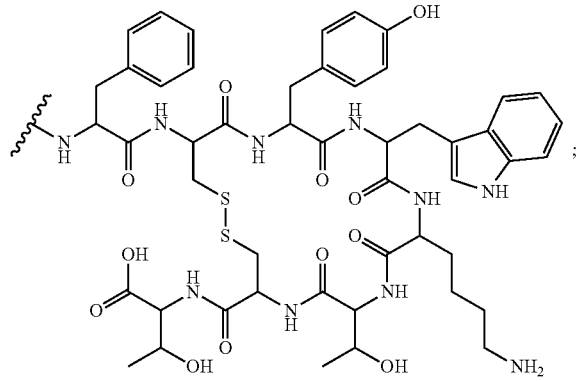 [SMILES: *NC(Cc1ccccc1)C(=O)NC1CSSCC(C(=O)NC(C(=O)O)C(C)O)NC(=O)C(C(C)O)NC(=O)C(CCCCN)NC(=O)C(Cc2c[nH]c3ccccc23)NC(=O)C(Cc2ccc(O)cc2)NC1=O]

and

LINKER is a linker group as described in WO2008139207 or a synthetic linker group of formula -(A)$_m$- wherein each A is independently —CR$_r$, —CR=CR—,

—CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a C$_{4-8}$cycloheteroalkylene group, a C$_{4-8}$cycloalkylene group, a C$_{5-12}$arylene group, or a C$_{3-12}$heteroarylene group, an amino acid, a sugar or a monodisperse polyethyleneglycol (PEG) building block; each R is independently chosen from H, C$_{1-20}$alkyl, C$_{2-4}$alkenyl, C$_{2-4}$alkynyl, C$_{1-4}$alkoxy C$_{1-20}$alkyl or hydroxy C$_{1-20}$alkyl; m is an integer of value 1 to 20.

The present invention provides an alkyne linked [Tyr³] octreotate analogue of Formula (IV) as described above wherein R₁ and R₂ are each as described above for Formula (IV) and LINKER is -(polyethylene glycol)ₙ-;

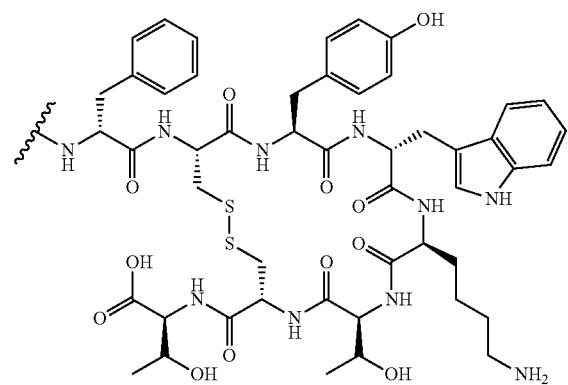

wherein n is an integer from 1-20; preferably, n is an integer from 1-10; more preferably, n is an integer from 1-6.

In one embodiment of the invention, R₂ compound of Formula (IV) as described above is:

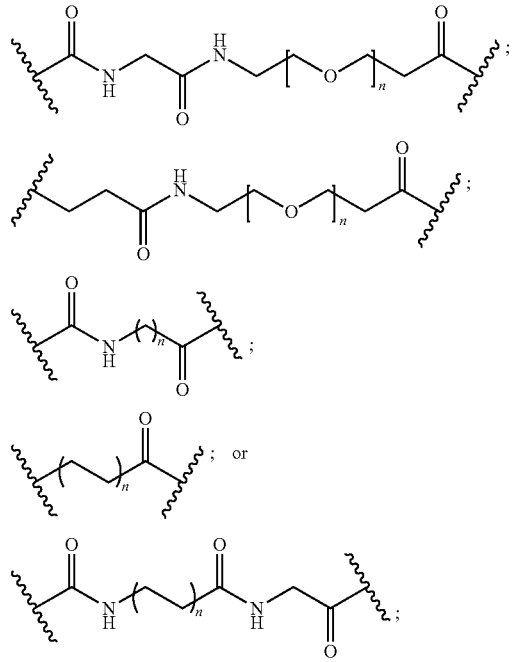

The present invention provides an alkyne linked [Tyr³] octreotate analogue, G-PEG-TOCA, of Formula (Ia):

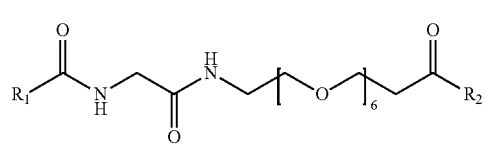

(Ia)

wherein:

R₁ is

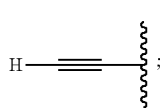

and

R₂ has the following structure:

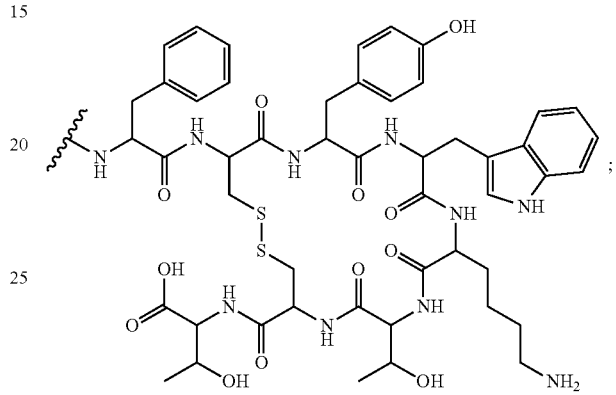

preferably R₂ has the following structure:

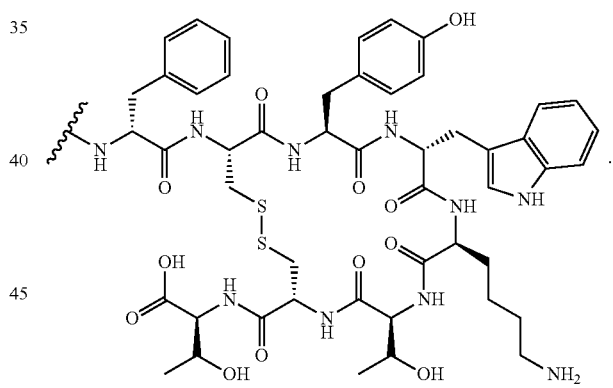

The present invention provides an alkyne linked [Tyr³] octreotate analogue, E-PEG-TOCA, of Formula (2a):

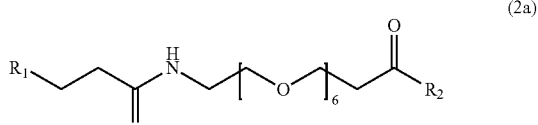

(2a)

wherein R₁ and R₂ are each as described above for the compound of Formula (1a).

The present invention provides an alkyne linked [Tyr³] octreotate analogue, G-TOCA (3a):

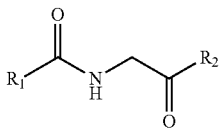

(3a)

wherein $R_1$ and $R_2$ are each as described above for the compound of Formula (1a).

The present invention provides an alkyne linked [Tyr³] octreotate analogue, E-TOCA (4a):

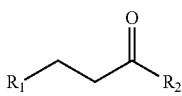

(4a)

wherein $R_1$ and $R_2$ are each as described above for the compound of Formula (1a).

The present invention provides an alkyne linked [Tyr³] octreotate analogue, βAG-TOCA (5a):

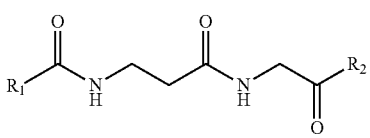

(5a)

wherein $R_1$ and $R_2$ are each as described above for the compound of Formula (1a).

The present invention provides an alkyne linked [Tyr³] octreotate analogue, βAG-[W-c-(CTFTYC)K] (6a):

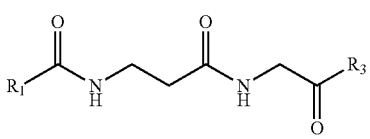

(6a)

wherein $R_1$ is as described above for the compound of Formula (1a) and $R_3$ is:

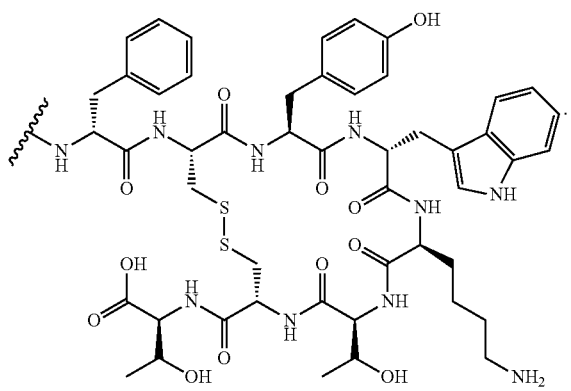 [SMILES: *N[C@H](Cc1ccccc1)C(=O)N[C@H]1CSSC[C@@H](C(=O)N[C@H](C(=O)O)C(C)O)NC(=O)[C@H](C(C)O)NC(=O)[C@H](CCCCN)NC(=O)[C@@H](Cc2c[nH]c3ccccc23)NC(=O)[C@H](Cc2ccc(O)cc2)NC1=O]

Synthesis

A 2-[¹⁸F]fluoroethyl triazole linked [Tyr³]Octreotate analogue(s) of the present invention and an alkyne linked [Tyr³]Octreotate analogue(s) of the present invention can be prepared by methods known in the art (WO2010/026388 which is hereby incorporated in its entirety by reference) and by those methods exemplified below.

The introduction of a PET radioisotope (i.e., any positron-emitting radioisotope) as described herein may be introduced into a compound of Formulae (I), (II), (III) and a 2-fluoroethyl triazole linked [Tyr³]Octreotate analogue either prior to formation of the triazole moiety or after the formation of the triazole moiety by any means known in the art (e.g. WO 2010/026388). A SPECT radioisotope can be introduced into a molecule of Formulae (I) or (II), each as described herein, in a likewise manner.

According to the present invention, a method of making a 2-[¹⁸F]fluoroethyl triazole linked [Tyr³]Octreotate analogue(s) of the present invention comprises the step of reacting an alkyne linked [Tyr³]Octreotate analogue(s) with 2-[18F]Fluoroethylazide under copper catalyzed click chemistry conditions to form the corresponding 2-[¹⁸F] fluoroethyl triazole linked [Tyr³]octreotate analogue, each as described herein.

In one embodiment of the invention, the synthesis of 2-[¹⁸F]fluoroethyl triazole linked [Tyr³]Octreotate analogue is automated. [¹⁸F]-radiotracers may be conveniently prepared in an automated fashion by means of an automated radiosynthesis apparatus. There are several commercially-available examples of such apparatus, including Tracerlab™ and FASTlab™ (both from GE Healthcare Ltd.). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The present invention therefore provides in another aspect a cassette for the automated synthesis of the PET radiotracer as defined herein comprising:

(i) a vessel containing an alkyne-linked [Tyr3]octreotate analogue, as described herein; and (ii) a vessel containing an azide capable of undergoing a click chemistry reaction with an alkyne-linked [Tyr³]octreotate analogue of vessel (iii) (e.g. tosylethyl azide in a solution of MeCN, DMSO or DMF); and (iii) adding the contents of said vessel (ii) to a suitable source of ¹⁸F.

According to the present invention, a cassette of the present invention may, optionally, further comprise one or more of the following:

(iv) a QMA cartridge;

(v) QMA eluent to release the trapped fluorine-18 consisting of K222, MeCN, water and a base (e.g., TBAHCO₃, K₂CO₃, Cs₂CO₃);

(vi) a vessel containing a copper catalyst (e.g., copper (I) catalyst; copper sulphate in an aqueous solution);

(vii) a vessel containing Na-ascorbate (preferably, in sodium acetate buffer solution at pH 5.0);

(viii) a vessel containing a copper (I) stabilising ligand (e.g., BPDS);

(ix) a line directed to an HPLC system; and (ix) an ion-exchange cartridge for removal of excess ¹⁸F.

EXAMPLES

Reagents and solvents were purchased from Sigma-Aldrich Co. Ltd. (Gillingham, United Kingdom) and VWR International Ltd UK, and used without further purification. BPDS (9) was purchased from Pfaltz & Bauer Inc. Waterbury, USA. [$^{18}$F]-AlF-NOTA was synthesized according to Layerman P, et al., *J Nucl Med.* 2010; 51:454-461. [$^{68}$Ga]-DOTATATE was purchased from Covidien (UK) Commercial Ltd (Gosport, UK).

MALDI-TOF were measured at The London School of Pharmacy on a Finnigan Lasermat 2000 instrument. Analytical HPLC was carried out using a Beckman Gold instrument with Karat32 software or Laura software. The radio HPLC system was a Beckman System Gold instrument equipped with a γ detector (Bioscan Flow-count). A Phenomenex Luna C18(2) column (50×4.6 mm, 3 μm; flow rate 1 mL/min) was used for analytical HPLC. A semipreparative column (Phenomenex Luna C18, 100×10 mm, 5 μm, 110A; flow rate of 3 mL/min) was used for the final purification of the peptides. The following mobile phase system was used for analytical HPLC: solvent A, water/TFA (0.1%); solvent B, acetonitrile/TFA (0.1%); linear gradient of 5-80% solvent ACN/0.1% TFA over 15 min. Non-radioactive compounds were purified using a preparative HPLC (Agilent1200, column Phenomenex Luna C18(2), 75×30 mm, 5 μm, flow rate 15 mL/min). To separate samples for log D calculations a MSE Micro Centaur centrifuge apparatus was used, Gamma counts were carried out using a Wallac 1282 Compugamma Universal gamma counter and results recorded using the EdenTerm v1.2 software. [$^{18}$F]Fluoride was produced by a cyclotron (PET Trace, GE Medical systems) using the $^{18}$O(p,n)$^{18}$F nuclear reaction with 16.4 MeV proton irradiation of an enriched [$^{18}$O]H$_2$O target.

Abbreviations:
ACN: Acetonitrile
DCM: Dichloromethane
DIPEA: Diisopropylethylamine
Fmoc: 9-Fluorenylmethyloxycarbonyl
HBTU: O-Benzotriazol-1-yl-N,N,N',N'-tetramethyluronium hexafluorophosphate
HOBt: 1-Hydroxybenzotriazole
NMP: 1-Methyl-2-pyrrolidinone
PyBOP: (Benzotriazol-1-yloxy)tripyrrolidinophosphonium hexafluorophosphate
SASRIN: Super acid sensitive resin
TFA: Trifluoroacetic acid
TIS: Triisopropylsilane Example 1

General Method for the Synthesis of [19F]Fluoroethyl Triazole Peptide Standards (a) To a Wheaton vial charged with copper powder (20 mg, –40 mesh) was added an alkyne linked [Tyr$^3$]octreotate analogue (alkyne-peptide) (5 mg) in a solution of DMF/H$_2$O (1:1 v/v (60 μL)). To this was added [$^{19}$F]fluoroethyl azide (1.5 eq, 0.354 M in DMF)(Glaser, M.; and Arstad, E., *Bioconjugate Chemistry* 2007, 18, (3), 989-993). The reaction was left stirring at room temperature for 30 minutes and then quenched with 0.1 mL of 20% MeCN/H$_2$O 0.1 TFA before injection for purification using the Agilent preparative HPLC. All analogues were isolated using a gradient of 20-80% MeCN/H$_2$O 0.1% TFA over 30 minutes. Mass spectrometry result are summarized in Table 1 below.

TABLE 1

Mass spectrometry of the $^{19}$F-standards

| Triazole | Isolated Yield | MALDI-TOF data |
|---|---|---|
| [$^{19}$F]1b | 35% | found [M + Na] m/z 1604.7 $C_{71}H_{99}FN_{15}O_{21}S_2Na$ requires m/z 1604.8 |
| [$^{19}$F]2b | 44% | found [M + Na]$^+$ m/z 1575.8 $C_{71}H_{100}FN_{14}O_{20}S_2Na$ requires m/z 1575.8 |
| [$^{19}$F]3b | 37% | found [M + Na]$^+$ m/z 1269.0 $C_{56}H_{70}FN_{14}O_{14}S_2Na$ requires m/z 1269.4 |
| [$^{19}$F]4b | 56% | found [M + Na]$^+$ m/z 1240.5 $C_{56}H_{71}FN_{13}O_{13}S_2Na$ requires m/z 1240.4 |
| [$^{19}$F]5b | 29% | found [M + Na]$^+$ m/z 1340.4 $C_{59}H_{75}FN_{15}O_{15}S_2Na$ requires m/z 1340.5 |
| [$^{19}$F]6b | 38% | found [M + Na]$^+$ m/z 1340.5 $C_{59}H_{75}FN_{15}O_{15}S_2Na$ requires m/z 1340.5 |

(b) DMF only. The [$^{19}$F]standards, [$^{19}$F]-1b-6b, were also synthesised using copper powder, and DMF as solvent. For compounds [$^{19}$F]-1a and [$^{19}$F]-3a, the use of DMF as the sole solvent proceeded slowly (>3 hours). Addition of water (DMF:H$_2$O (3:2)) enhanced the rate of reaction with reaction completion within 15 minutes.

Example 2a

General Method for the Synthesis of 2-[$^{18}$F]Fluoroethyl Triazole Linked [Tyr$^3$]Octreotate Analogue As illustrated in Scheme 1 below, a radiolabeled [Tyr$^3$] octreotate analogue of the invention may be prepared by labelling an alkyne linked [Tyr$^3$]octreotate analogues by means of a copper catalysed azide-alkyne cycloaddition reaction (CuAAC) to form a 1,4-substituted triazole using the reagent 2-[$^{18}$F]fluoroethyl azide, i.e. a 2-[$^{18}$F]fluoroethyl triazole linked [Tyr$^3$]Octreotate analogue of the invention. An unexpected variability in reactivity during the CuAAC reaction was observed for each alkyne analogue investigated.

Scheme 1: The reaction pathway to the $^{18}$F-labelled triazoles: 1a, 2a, 3a, 4a 5a and 6a, each as described herein.

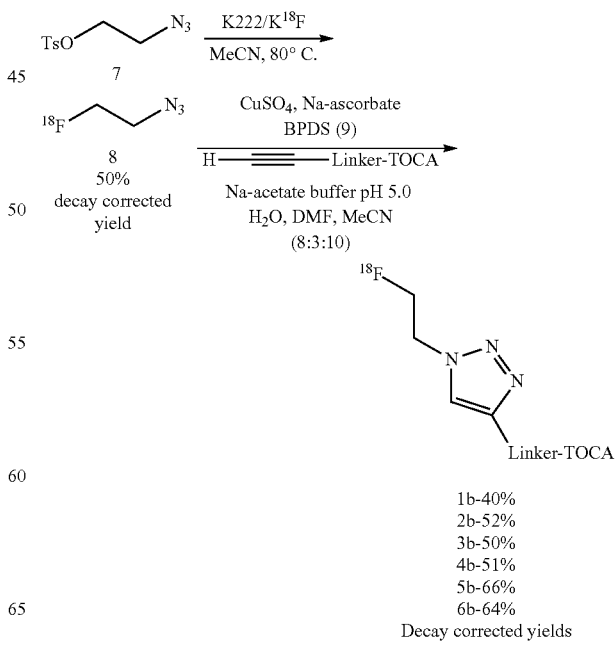

1b-40%
2b-52%
3b-50%
4b-51%
5b-66%
6b-64%

Decay corrected yields

-continued

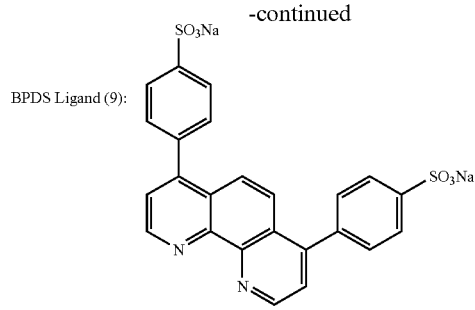

BPDS Ligand (9):

Example 2b

Alkyne Preparation

Five alkyne functionalised octreotate analogues (FIG. 1) were synthesized in a manner analogous to the synthesis of βAB-TOCA (5a) described below. A scrambled peptide (6b) (FIG. 1) was designed as a negative control to show no specificity to the somatostatin receptor. The linkers between the octreotate and the alkyne functionality were chosen to complement the peptide and for ease of synthesis. Two analogues were designed containing polyethylene glycol groups ((1a) and (2a)). The octreotate alkynes (1a-5a) and scrambled analogue (6a) were labelled using [$^{18}$F]fluoroethyl azide (8) (Scheme 1).

Example 2b.1

Synthesis of βAB-TOCA (5a)

2b.1.1 Synthesis of propynoyl-β-Ala-OH

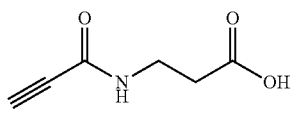

MW = 141.1
EM = 141.0
MF = C6H7NO3

Propiolic acid (3.00 mmol, 184 μL) was added to a solution of H-β-Ala-OMe HCl salt (3.00 mmol, 419 mg), PyBOP (3.00 mmol, 1.56 g) and DIPEA (9.00 mmol, 1.53 mL) dissolved in NMP (5 mL). The reaction mixture was shaken for 30 min then diluted with water/0.1% TFA and loaded onto a preparative HPLC column for purification affording propynoyl-β-Ala-OMe.

Propynoyl-β-Ala-OMe was dissolved in ACN/water/0.1% TFA (200 mL) and the solution adjusted to pH 11 using 0.1M NaOH. The solution was stirred for 1 hr and then reduced in vacuo. The residue (50 mL) was injected onto a preparative HPLC column for product purification.

Purification and Characterisation

Purification by preparative HPLC (gradient: 0% ACN/0.1% TFA over 60 min) afforded 260 mg (61% based on 3 mmol starting material) pure propynoyl-β-Ala-OH.

The purified material was analysed by analytical LC-MS (gradient: 0-15% ACN/0.1% TFA over 5 min, $t_R$: 0.29 min. found m/z: 142.3, expected MH$^+$: 142.0).

2b.1.2 Assembly of H-Gly-[Tyr$^3$]-Octreotate on Solid Support

The peptidyl resin H-Gly-D-Phe-Cys(Trt)-Tyr(tBu)-D-Trp(Boc)-Lys(Boc)-Thr(tBu)-Cys(Trt)-Thr(tBu)-Polymer was assembled using standard peptide synthesis procedures. The peptidyl resin H-Gly-D-Phe-Cys(Trt)-Tyr(tBu)-D-Trp(Boc)-Lys(Boc)-Thr(tBu)-Cys(Trt)-Thr(tBu)-Polymer was assembled on the commercially available CEM Liberty microwave peptide synthesizer using Fmoc chemistry starting with 0.25 mmol Fmoc-Thr(tBu)-SASRIN resin. 1.0 mmol amino acid was applied in each coupling step (5 min at 80° C.) using 0.9 mmol HBTU/0.9 mmol HOBt/2.0 mmol DIPEA for in situ activation. Fmoc was removed by treatment of the resin with a solution of 20% piperidine in NMP.

2b.1.3 Synthesis of propynoyl-β-Ala-Gly-[Tyr$^3$]-Octreotate (i.e., βAB-TOCA (5a))

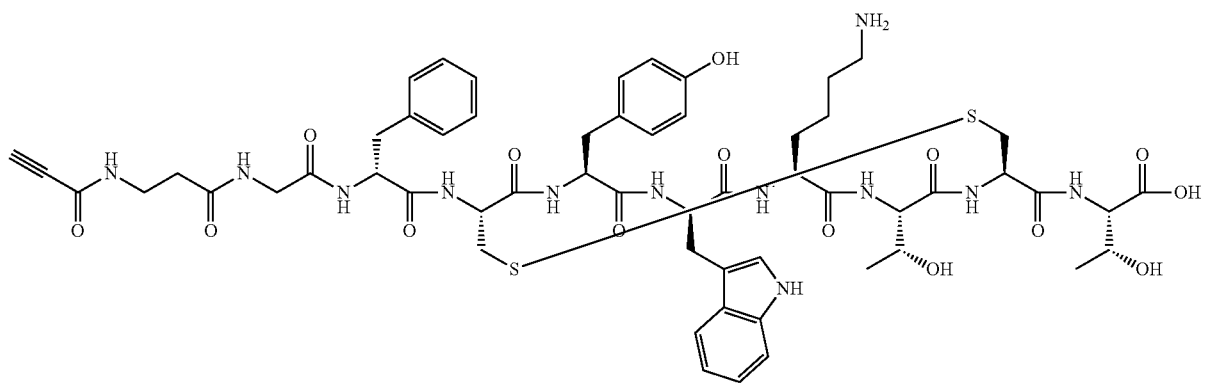

MW = 1229.4
EM = 1228.5
MF = C57H72N12O15S2

Propynoyl-β-Ala-OH (0.50 mmol, 71 mg, described above in 2b.1.1) and PyBOP (0.500 mmol, 260 mg) were dissolved in NMP (5 mL) and added to the Octreotate resin (0.25 mmol, described above in 2b.1.2). DIPEA (2.00 mmol, 340 μL) was added and the mixture shaken for 90 min. The reagents were removed by filtration and the resin washed with NMP, DCM and diethyl ether and dried.

The simultaneous removal of the side-chain protecting groups and cleavage of the peptide from the resin was carried out in TFA (100 mL) containing 2.5% TIS and 2.5% water for 90 min. The resin was removed by filtration, washed with TFA and the combined filtrates evaporated in vacuo. Diethyl ether was added to the residue, the formed precipitate washed with diethyl ether and dried. The dry precipitate was dissolved in 50% ACN/water and left over night in order to remove remaining Trp protecting groups. The solution was then lyophilised affording 294 mg (96%) crude propynoyl-β-Ala-Gly-D-Phe-Cys-Tyr-D-Trp-Lys-Thr-Cys-Thr-OH.

2,2'-Dithiodipyridine (0.27 mmol, 59 mg) dissolved in ACN (0.75 mL) was added in three equal portions to crude propynoyl-β-Ala-Gly-D-Phe-Cys-Tyr-D-Trp-Lys-Thr-Cys-Thr-OH (294 mg) dissolved in ACN/water/0.1% TFA (300 mL) and the solution shaken for 30 min. The reaction mixture was loaded onto a preparative HPLC column for product purification Purification and Characterisation Purification by preparative HPLC (gradient: 20-40% ACN/0.1% TFA over 60 min) afforded 140 mg (48%) pure propynoyl-β-Ala-Gly-[Tyr$^3$]-Octreotate.

The purified material was analysed by analytical LC-MS (gradient: 20-30% ACN/0.1% TFA over 5 min, $t_R$: 2.49 min. found m/z: 1229.5, expected MH$^+$: 1229.5).

Radiochemistry

Example 3

Preparation of 2-[$^{18}$F]Fluoroethylazide (8)

The method used to synthesise 8 was slightly modified to that employed by Glaser et al. (Glaser, M., et al., *Bioconjugate Chemistry* 2007, 18, (3), 989-993; Demko, Z. P., et al., *Angewandte Chemie-International Edition* 2002, 41, (12), 2113-2116). The use of KHCO$_3$ instead of K$_2$CO$_3$ during the [$^{18}$F]fluoride drying step gave more consistent isolated yields after purification by distillation, due to the enhanced stability of the precursor, 7 using the milder base.

To a mixture of Kryptofix 222 (5 mg, 13.3 μmmol), potassium hydrogencarbonate (1.4 mg, 16.7 in 100 μL water), and acetonitrile (0.5 mL) was added [$^{18}$F]fluoride (5-15 mCi) in water (0.1-1 mL). The solvent was removed by heating at 100° C. under a stream of nitrogen (100 mL/min). Afterwards, acetonitrile (0.5 mL) was added, and the distillation was continued. This procedure was repeated twice more. After cooling to room temperature, a solution of 2-azidoethyl-4-toluenesulfonate (7) (1.3 μL, 6.5 μmol)(Glaser, M.; et al., *Bioconjugate Chemistry* 2007, 18, (3), 989-993; Demko, Z. P.; et al., *Angewandte Chemie-International Edition* 2002, 41, (12), 2113-2116) in anhydrous acetonitrile (0.2 mL) was added. The reaction mixture was stirred for 15 min at 80° C. [$^{18}$F]8 was distilled at 130° C. into a trapping vial containing acetonitrile (30 μL)(Arstad, E., WO2008/015391A1). Compound [$^{18}$F]8 was collected with radiochemical yields between 50-55% (decay-corrected).

Generation of 2-[$^{18}$F]fluoroethyl azide for the preparation of samples via click chemistry, subsequently used for in vivo studies, was carried out on a remotely controlled apparatus built at Hammersmith Imanet. The system enables the use ~200-300 mCi of [$^{18}$F]fluoride as starting activity. Radiochemical yields (decay corrected) of isolated [$^{18}$F]fluoroethyl azide using this system range from 19-26%. However, the generation of 2-[$^{18}$F]fluoroethyl azide can be achieved by other means known in the art (Glaser, M.; et al., *Bioconjugate Chemistry* 2007, 18, (3), 989-993; Demko, Z. P.; et al., *Angewandte Chemie-International Edition* 2002, 41, (12), 2113-2116; WO2008/015391A1).

Example 4

General Method for Labelling

For alkynes 1a, 2a and 4a: To a solution of copper (II) sulfate pentahydrate (4 eq) in water (25 μL) was added sodium L-ascorbate (4.4 eq) in 25 μL of sodium acetate buffer solution (pH 5.0, 250 mM) under N$_2$ followed by BPDS (9) (5 eq) in 25 μL of water. For alkynes 3a and 5a, CuSO$_4$ (2 eq), Na-ascorbate (2.2 eq), and BPDS (9) (4 eq) were used.

A solution of [$^{18}$F]8 in MeCN (100 μL) was added followed by the alkyne (2 mg) in DMF (30 μL) and the reaction carried out at room temperature (see Table 2 for optimal reaction time). The reaction was then diluted with H$_2$O 0.1% TFA (100 μL) and purified by reverse phase preparative HPLC using the gradient stated in Table 2. The HPLC fraction was then diluted with H$_2$O (15-19 mL) and loaded onto a tC18 light SPE cartridge. The product was eluted with ethanol in 100 μL fractions and made up to a solution of 10% ethanol/PBS buffer solution (pH 7.0) with >98% RCP.

TABLE 2

HPLC solvents MeCN/H$_2$O 0.1% TFA ("B"), 3 mL/min using a Luna C18 5 u, 100 × 10 mm, 5 micron, 110 A

| Alkyne | Reaction time | HPLC gradient | Pseudo-Specific Activity (GBq/μmol) | Isolated yield (%) (decay corrected) |
|---|---|---|---|---|
| 1a | 30 min | 25-50% B over 30 min | 4.8 | 40 |
| 2a | 15 min | 15-40% B over 25 min | 5.9 | 52 |
| 3a | 5 min | 25-50% B over 20 min | 5.9 | 50 |
| 4a | 30 min | 25-50% B over 25 min | 8.4 | 51 |
| 5a | 5 min | 25-50% B over 25 min | 11.2 | 66 |
| 6a | 15 min | 25-50% B over 25 min | 12.3 | 64 |

Example 5

Octanol/Phosphate Buffer Partition Co-efficient Measurements (Log D)

The octanol/PBS partition coefficients were determined using the shake flask method. Both solvents were presaturated with each other by shaking together for 5 min. To a solution of 500 μL of both octanol and PBS was added 20 μL of radiolabelled ligand in EtOH (n=3). The solutions mixtures were shaken in a rotamixer for 5 minutes. After equilibration the mixtures were centrifuged (10 min at 13,000 rpm) to achieve good separation. Samples from each layer (25 µL) were taken and measured in a γ counter and Log D was calculated according to the formula:

$$\log D = \log(\text{cpm in octanol layer/cpm in aqueous layer}).$$

Log D values were measured using the $^{18}$F-labelled triazole. As expected the Log D values for the analogues 1b and 2b were the lowest due to the PEGylation, and the analogue with the highest Log D value was 4b (Table 3). The receptor affinities for [$^{18}$F]1b-6b were determined using a competitive binding assay in AR42J tumours cells with [$^{111}$In]-OctreoScan as the labeled radiotracer. The half-maximal inhibitory concentration (IC$_{50}$) values were calculated and the results of the displacement curves are summarised (Table 3). As a reference peptide, the IC$_{50}$ value was measured for Octreotide and was found to be 14.7±7.7 nM. The IC$_{50}$ values for the octreotate analogues were found to be comparable or lower than octreotide, indicating high binding affinity for the somatostatin receptor; all showed high binding affinity to the receptor in the nanomolar range. The introduction of the fluoroethyl triazole moiety decreased the affinity for [$^{19}$F]-2b,3b,4b and 5b but not significantly, the values were still below or comparable to octreotide. In this study the compound [$^{19}$F]-5b showed the highest affinity with an IC$_{50}$ value of 1.6±0.2 nM. PEGylation of the peptides, through the addition of six sequential ethylene glycol groups, appeared not to significantly affect the overall affinity of [$^{18}$F]-1b and [$^{19}$F]-2b giving IC$_{50}$ values of 2.9±1.3 nM and 13.2±7.8 nM, respectively. In comparison [$^{19}$F]-6b, which contained a scrambled amino acid sequence, showed low affinity giving an IC$_{50}$ value >10 mM. This result showed that our analogues are specifically binding to the somatostatin receptor.

TABLE 3

Competitive binding assay IC$_{50}$ values using 1a-5a and [$^{19}$F]-1b-6b displacing [$^{111}$In]-DTPA-Octreotide on AR42J tumour cells and Log D values of [$^{18}$F]-1b-6b.

| Peptides | Alkyne analogue (a) IC$_{50}$ (nM) | Triazole analogue (b) IC$_{50}$ (nM) | Control | Log D of $^{18}$F-triazole |
|---|---|---|---|---|
| 1 | 5.3 ± 0.75 | 10.8 ± 5.9 | | −2.68 |
| 2 | 5.1 ± 2.1 | 13.2 ± 7.8 | | −2.77 |
| 3 | 1.4 ± 0.1 | 4.0 ± 1.4 | | −1.83 |
| 4 | 1.8 ± 0.8 | 2.9 ± 1.3 | | −1.5 |
| 5 | 1.0 ± 0.3 | 1.6 ± 0.2 | | −2.26 |
| 6 | | >10.0 (mM) | | −1.14 |
| Octreotide | | | 14.7 ± 7.7 | |

N.B. (n = 4 for each concentration and assay repeated three times). Log D partition co-efficient measurements 1b-5b (n = 3), 6b (n = 6). IC$_{50}$ values of AlF-NOTA-Octreotide, Ga-NOTA-Octreotide found by Laverman, P., et al. (*Journal of Nuclear Medicine 51*, (3), 454-461) were 3.6 ± 0.6, 13.0 ± 3.0 nM respectively.

Example 6

In Vitro Receptor Binding Determination

To determine the binding affinity of [$^{19}$F]-fluoroethyltriazole-[Tyr]$^3$-octreotate analogues ($^{19}$F-1b-6b), and the alkyne-octreotate analogues (1a-6a) an in vitro assay was done using a modification of the method previously reported by Hofland and co-workers (Hofland, L. J.; et al., *Endocrinology* 1995, 136, (9), 3698-706). AR42J cells (5×10$^4$) were seeded in 24-well plates, washed twice in PBS and incubated with increasing concentrations (0, 0.01, 0.1, 1, 1.0, 10, 100, 1000 and 10000 nM) of the compound being analysed for 10 min at room temperature, allowing for sufficient time for binding to occur under these experimental condition (Scemama, J. L.; et al., *Gut* 1987, 28 Suppl, 233-6). The plates were then incubated for a further 30 min with [$^{111}$In] OctreoScan (Covidien, Gosport, UK: (50,000 cpm per well). A final volume of 0.25 mL of incubation buffer per well was used. The incubation buffer consisted of 10 mM HEPES, 5.0 mM, MgCl$_2$ 6H$_2$O, 1.0 mM bacitracin, 1% BSA, and the final pH was adjusted to 7.4. At the end of the incubation, the plates were washed three times in ice cold incubation buffer and solubilised in 0.2N NaOH solution. The contents of each well were then transferred to counting tubes and samples counted using a gamma-counter (Biosoft, Ferguson, Mo.). Each concentration was performed in quadruple and the experiment repeated three times. Results are expressed as a percentage of control (first four wells treated with only labelled [$^{111}$In]OctreoScan). The IC$_{50}$ values were calculated from the fitted sigmoidal displacement curve using GraphPad Prism software (version 4.00) for Windows, GraphPad Software, Inc).

Example 7

Use of Copper Wire as Catalyst

The use of copper wire as an alternative source of catalytic Cu(I) was investigated. The experiments were carried out using 3a due to its enhanced reactivity compared to other analogues using the CuSO$_4$/Na-ascorbate method. It was found that pre-mixing the copper wire and alkyne then heating before addition of 8 showed the reaction to be complete within 5 minutes (Table 4, entry 2). Without pre-mixing the two components, the click reaction took longer to reach completion (Table 4, entry 1). Other pH buffer systems (Table 4, entries 4,5 and 6) were also applied, but all proved inferior to the sodium acetate buffer solution (pH 5.0, 250 mM) (Table 4, entry 1). CuSO$_4$ and BPDS (9) were added to the reaction using copper wire, the rationale behind this approach being that the added CuSO$_4$ would improve the comproportionation reaction by increasing the concentration of available Cu(II) (Gopin, A., et al., *Bioconjugate Chemistry* 2006, 17, 1432-1440; Bonnet, D., et al., *Bioconjugate Chemistry* 2006, 17, 1618-1623). The ligand (9) as previously mentioned, was added to stabilise the Cu(I) species. The strategy worked well and showed improvement in yields at room temperature (Table 4, entry 7). To establish whether this was a tandem effect, reactions were carried out to investigate both additional reagents separately (Table 4, entries 7,8). It appears that that both reagents affect the rate to some extent but used together they have a greater impact on the rate of the reaction. MonoPhos™ (Campbell-Verduyn, L. S., et al., *Chemical Communications* 2009, (16), 2139-2141) was investigated as an alternative ligand, but proved less efficient in the reaction (Table 4, entry 10).

TABLE 4

Copper wire catalysed experiments using alkyne 3a
(Analytical radiochemical yield by HPLC)

| | Reaction Temperature | pH | Solvents (v/v) | Pre-activation time (min) | Other additives | Analytical Yield (%) at: | | |
|---|---|---|---|---|---|---|---|---|
| | | | | | | 5 min | 15 min | 30 min |
| 1 | 80° C. | 5.0 | DMF/AB (1:3) | 0 | — | 52 | 95 | |
| 2 | 80° C. | 5.0 | DMF/AB (1:3) | 30 | — | >98 | | |
| 3 | rt | 5.0 | DMF/AB (1:3) | 150 | — | 0 | 7 | 30 |
| 4 | 80° C. | 6.0 | DMF/PB (1:3) | 0 | — | 4 | | |
| 5 | 80° C. | 4.0 | DMF/FB (1:3) | 0 | — | 3 | | |
| 6 | 80° C. | 8.0 | DMF/TB (1:3) | 0 | — | 2 | | |
| 7 | rt | 5.0 | DMF/AB (1:3) | 0 | 40 mol % $CuSO_4$, BPDS (9) (2 eq) | 67 | >98 | |
| 8 | rt | 5.0 | DMF/AB (1:3) | 0 | 40 mol % $CuSO_4$, | 0 | 0 | 48 |
| 9 | rt | 5.0 | DMF/AB (1:3) | 0 | BPDS (9) (2 eq) | 35 | 54 | >98 |
| 10 | rt | 5.0 | DMSO/AB (7:3) | 0 | MonoPhos Ligand (2 eq) | 0 | 0 | 0 |

All buffers are 250 mM concentrations. Sodium acetate buffer (AB) pH 5.0; Sodium phosphate buffer (PB) pH 6.0; Ammonium formate buffer (FB) pH 4.0; Tris buffer (TB) pH 8.0. Each experiment contained 100-120 mg of a copper wire coil (rt = room temperature).

Results

The alkyne linked [Tyr³]octreotate analogues, G-TOCA (3a) and βAG-TOCA (5a) have been identified to be highly reactive in the click reaction showing complete conversion to the 2-[18F]fluoroethyl triazole linked [Tyr³]Octreotate analogues FET-G-TOCA (3b) and FET-βAG-TOCA (5b) under mild conditions and with short synthesis times (5 minutes at 20° C.). As well as ease of synthesis, in vitro binding to the pancreatic tumour AR42J cells showed that both FET-G-TOCA (3b) and FET-βAG-TOCA (5b) have high affinity for the somatostatin receptor with $IC_{50}$ of 4.0±1.4, and 1.6±0.2 nM respectively.

The variability in click reaction rates observed for the alkyne-peptides 1a-5a, can be attributed to the variation in linker, since the peptide moiety remains unchanged. The electronic property of the group adjacent to the terminal alkyne centre is believed to neither enhance nor reduce the rate of reaction (Hein, J. E., et al., *Chemical Society Reviews* 2010, (39), 1302-1315). Contrary to this, it has now been found that terminal alkynes directly substituted with an amide moiety (1a, 3a, 5a, 6a (FIG. 1)) had enhanced reactivity compared to those directly substituted with an ethyl-linked amide (2a and 4a, (FIG. 1)). Similar results were found by Li et al. (*Tetrahedron Letters* 2004, 45, 3143-3146) during their investigations of the 1,3-Huisgen cycloaddition reaction and separately by Golas et al. (*Macromolecular Rapid Communications* 2008, 29, 1167-1171) who investigated the effect of electron withdrawing groups and steric hindrance around the azide moiety on the rate of the CuAAC. Another factor to be taken into consideration along with the electronic nature of the alkyne is the size of the alkyne-peptide. Kinetically it would be expected that the larger the alkyne-peptide the slower the rate of reaction, which was found to be the case with the PEGylated analogues (1a, 2a). It can be seen that 1a reacts more slowly that 3a and 5a (Table 5, conditions B). Electronically they are similar, all being directly linked amide substituted terminal alkynes, but 1a contains six sequential ethylene glycol groups. It is possible that the PEG chain is surrounded by a bulky water cloud which could sterically hinder the alkyne functionality (Shiffman, M. L., *Current Hepatitis Reports* 2003, 2, 17-23). Alkynes 2a and 4a are comparable in the same respect (PEGylated vs. non-PEGylated); it was observed that 2a shows a slower rate of reaction during the CuAAC. Due to the slower rate of reaction and variation found using 1a and 2a during the click reaction, it was necessary to increase the concentration of reagents. Improvements were seen in the reproducibility and rate of reaction (Conditions D, Table 5). Analogues 1b-6b were isolated to give non-decay corrected yields of 3-7% (based on starting fluoride activity) after 90-120 minutes. Reaction rate was increased using higher temperatures with reaction times being reduced, but this led to significant by-product formation and made purification more difficult (Table 5, conditions C).

Figure 1A:
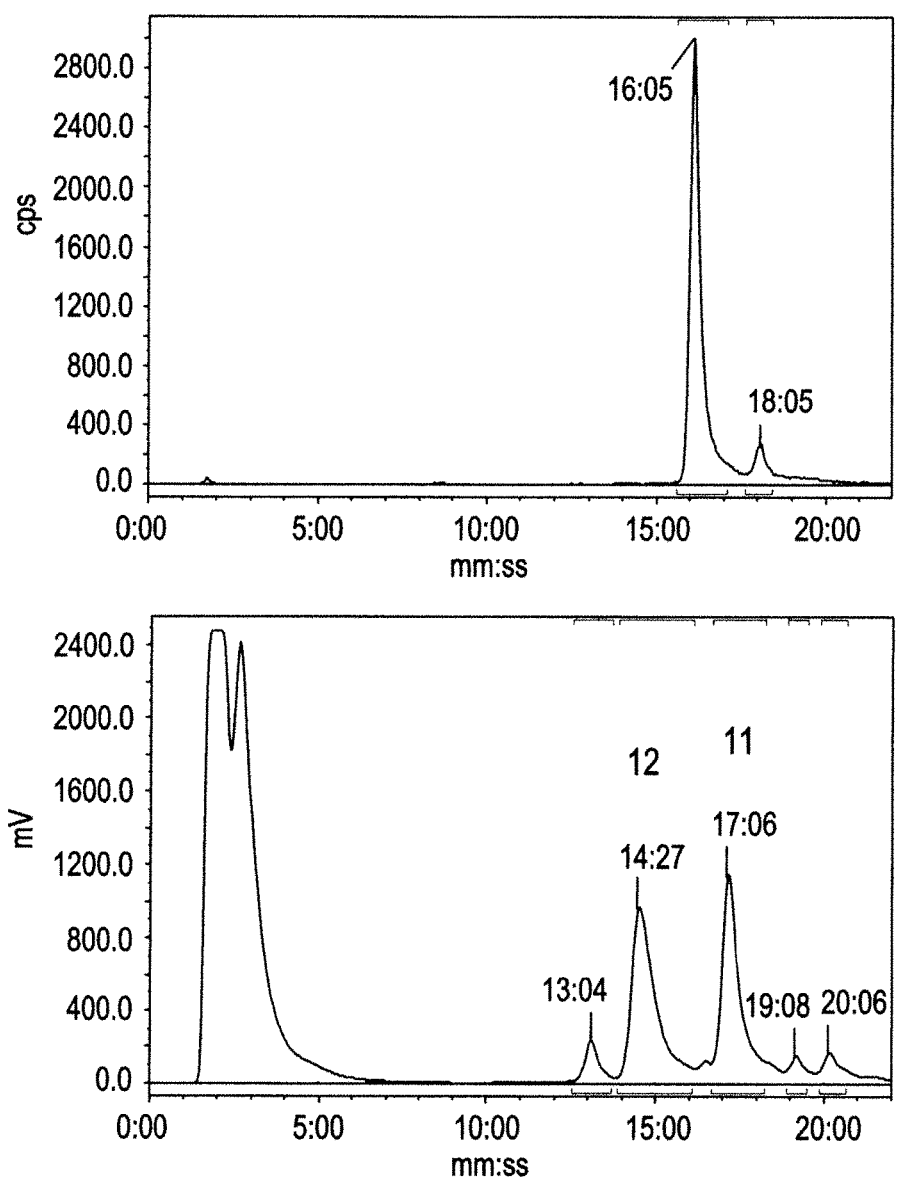
FIG. 1a depicts semi-preparative HPLC trace of the reaction mixture to synthesise 5b showing the by-products formed 11 and 12. Semi-preparative HPLC using a Luna C18 100×10 mm 5 micron, gradient 25-50% MeCN/H$_2$O 0.1% TFA. Top trace: Radioactivity channel 5b (retention time 16.05 min). Bottom trace: UV channel, λ 254 nm, the two by-products, 12 (retention time 14.27 min) and 11 (retention time 17.06 min).
Figure 3:
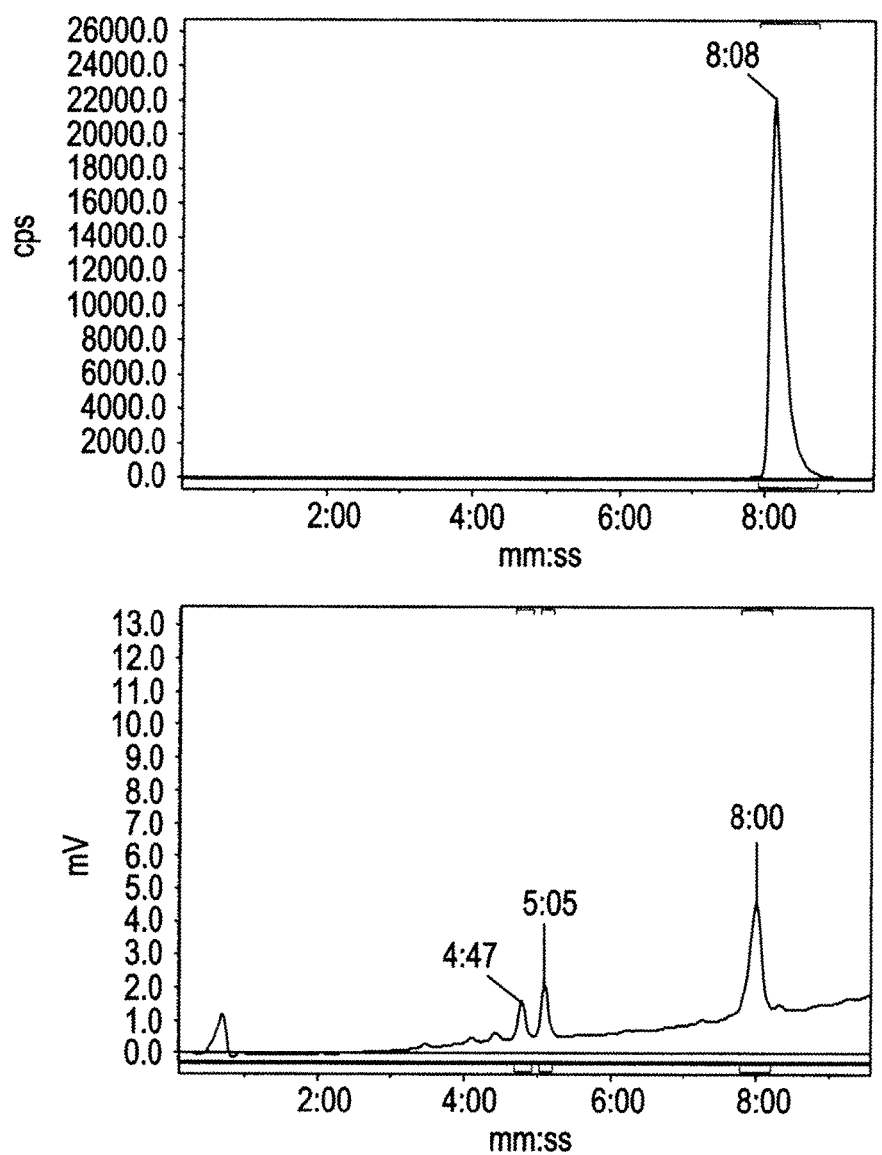
FIG. 3 depicts HPLC Analysis of FETE-PEG-TOGA (2b) carried out using a Phenomenex Luna C18(2) column (50×4.6 mm, 3 µm; flow rate 1 mL/min) using a gradient of 5-80% ACN/0.1% TFA over 15 min.

A general trend found during the click reaction with analogues 1a-6a were two stable by-products seen during HPLC monitoring. The two by-products 11 and 12 (Scheme 2, FIG. 1a) were isolated from the reaction media using 5a (FIG. 1). They were separated, collected and analysed by collision induced dissociation mass spectrometry (CID-MS). The more polar compound 12 was elucidated to be the alkyne precursor (5a) during CID-MS analysis. Although this was found to be the case, when the reaction mixture was admixed with 5a and assessed chromatographically, by-product 12 did not co-elute on the HPLC trace. It was found that reactions showing incomplete incorporation of 2-[¹⁸F] fluoroethyl azide (8) did not significantly proceed any further, even in the presence of 12, suggesting insufficient reactivity of this species in the CuAAC reaction. The by-product 11 was analysed and found to correspond to the 1-vinyl triazole (Scheme 2).

Scheme 2. Suspected pathway to form by-product 11

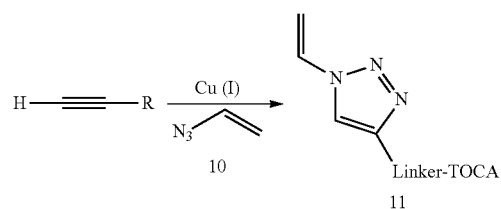

Presumably 11 was formed via the click reaction with azidoethene (10), which is suspected to be a by-product from an elimination mechanism in the initial labelling step. Kim et al. (*Applied Radiation and Isotopes* 2010, 68, 329-333) reported a similar occurrence using 4-tosyloxy-1-butyne; they observed elimination to form vinyl acetylene, which was then able to react with the azide in the click reaction. The main issue with by-product 11 is the similar retention time to the radiolabelled product during purification, making it difficult to obtain the highest yield possible as well as high specific radioactivity.

The experiments carried out using the $CuSO_4$/Na-ascorbate method were generally done using sodium acetate buffer (AB) at pH 5.0. When an experiment using 3a was carried out using distilled water the conversion to radiolabelled product was slower, showing 78% conversion at 5 min compared to >98% conversion using the buffered system.

A one-pot reaction was carried out in which distillation of 8 was avoided. The reaction was attempted with both 2a and 3a but both showed slower reaction rates presumably due to competing side reactions. Another variable that can affect the rate of reaction is the volume of 2-[$^{18}$F]fluoroethyl azide. A reaction carried out using conditions B (Table 5) with 2a and 50 µl of 2-[$^{18}$F]fluoroethyl azide (8) gave 84% conversion to 3b after 30 minutes. When using 100 µl of 8 under the same conditions no reaction was observed (Table 5).

It was found that using BPDS ligand (9) (Scheme 1), a Cu(I) stabilizing ligand (Gill, H. S., et al., *Journal of Medicinal Chemistry* 2009, 52, 5816-5825), greatly enhances the rate of the click reaction. The reaction was evaluated without any ligand. Reactions carried out with 4a without 9 (Table 5, conditions A) showed 14% conversion to the desired product but on addition of 9 (conditions B), gave 47% conversion. Using the same reagent concentrations but heating the reaction to 80° C. gave >98% conversion to 4b after 5 minutes (Table 5, conditions C); although the conversion to product at this temperature was excellent, an increase in by-products was observed, some of which co-eluted with 4b.

TABLE 5

Radiochemical Analytical Yields observed using HPLC analysis

| Alkyne | Analytical Yields (reaction time, min) | | | |
|---|---|---|---|---|
|  | Conditions A[a] | Conditions B[b] | Conditions C[c] | Conditions D[d] |
| 1a |  | 19% (30) | >98% (30) | >98% (30) |
| 2a |  | 0% (30) | 0% [(e)] (30) | >98% (30) |
| 3a |  | >98% (5) | >98% (5) |  |
| 4a | 14% (30) | 47% (30) | 97% (5) | >98% (30) |
| 5a |  | >98% (5) |  |  |
| 6a |  | 77% (30) |  | >98% (15) |

[a]Conditions A: Alkyne (2 mg), $CuSO_4$ (2 eq.), Na-ascorbate (2.2 eq), pH 5.0, rt
[b]Conditions B: Alkyne (2 mg), $CuSO_4$ (2 eq), Na-ascorbate (2.2 eq), 9 (4 eq), pH 5.0, rt
[c]Conditions C: Alkyne (2 mg), $CuSO_4$ (2 eq), Na-ascorbate (2.2 eq), 9 (4 eq), pH 5.0, 80° C.
[d]Conditions D: Alkyne (2 mg), $CuSO_4$ (4 eq), Na-ascorbate (4.4 eq), 9 (5 eq), pH 5.0, rt
[(e)] No alkyne remains in the reaction only the by-products are found in the UV trace.

In conclusion, five novel alkyne functionalised octreotate analogues were reacted in the click reaction with 2-[$^{18}$F] fluoroethyl azide. The most reactive alkynes were G-TOCA (3a) and βAG-TOCA (5a), showing complete conversion to the labelled triazole FET-G-TOCA (3b) and FET-βAG-TOCA (5b) in five minutes at room temperature using optimised conditions. As well as efficiency in the click reaction both analogues have shown high binding affinities to the somatostatin receptor.

Example 8

In Vitro Binding Assay

The affinity of a [$^{19}$F]fluoroethyltriazole-[Tyr$^3$]octreotate analogue of the present invention for somatostatin receptor subtype sstr-2, versus sstr-3 and sstr-4 as control low affinity receptor subtypes, was determined using a fluorometric imaging plate reader (FLIPR) assay. The assay involved measuring the [$^{19}$F]fluoroethyltriazole-[Tyr$^3$]octreotate induced activation of a calcium flux in sstr-2, 3 or 4—expressing Chem-1 cells (Millipore, St Charles, Mo., USA) that were pre-loaded with a calcium dye. Briefly, Chem-1 cells expressing specific sstr-subtype were seeded in 96 well plates at 50,000 cells/well and incubated in a 5% $CO_2$ incubator for 24 h. Cells were washed and loaded with Fluo-8-No-Wash $Ca^{2+}$ dye in GPCRProfiler™ Assay Buffer (Millipore) for 90 min at 30° C. in a 5% $CO_2$ incubator. Different concentrations of a [$^{18}$F]-fluoroethyltriazole-[Tyr$^3$]octreotate of the present or somatostatin (Sigma; positive control) were added followed by fluorescence determination. The assay was performed in agonist mode in duplicate. Antagonistic activity was not evaluated because of agonist activity. Fluorescence output was measured and data expressed as % maximal fluorescence signal after baseline correction. The half-maximal receptor activation for the various ligands was estimated by sigmoid dose response fitting using GraphPad Prism version 4.00 for Windows (GraphPad Software, San Diego Calif. USA).

Example 9

Animals and Tumor Models

Six to eight-week old female BALB/c nu/nu athymic mice were obtained from Harlan United Kingdom Ltd (Bicester, UK). High sstr-2 pancreatic tumor cell line AR42J (Taylor J. E., et al., 1994; 15:1229-1236) and low sstr-2 human colon cancer cell line HCT116 (LGC Standards, Middlesex, UK) were cultured, respectively, in F12K and RPMI1640 growth medium containing 10% (v/v) fetal bovine serum, 2 mmol/L L-glutamine, 100 units/mL penicillin, and 100 g/mL streptomycin and grown in a 5% $CO_2$ incubator at 37° C. Tumors were established by subcutaneous. injection of 100 µl of PBS containing $1 \times 10^6$ cells. All animal experiments were done by licensed investigators in accordance with the United Kingdom Home Office Guidance on the Operation of the Animal (Scientific Procedures) Act 1986 and within guidelines set out by the United Kingdom National Cancer Research Institute Committee on Welfare of Animals in Cancer Research (Workman, P., et al., *Br J. Cancer.* 2010; 102:1555-1577). Tumor dimensions were measured continuously using a caliper and tumor volumes were calculated by the equation: volume=$(\pi/6) \times a \times b \times c$, where a, b, and c represent three orthogonal axes of the tumor. Mice were used when their tumors reached ~200 mm$^3$.

Example 10

In Vivo Plasma Stability of FET-βAG-TOCA

FET-βAG-TOCA (~3.7 MBq) was injected via the tail vein into non-tumor bearing BALB/c nu/nu mice. Blood was obtained under general isofluorane anesthesia at 30 min post injection and plasma samples were prepared and immediately frozen on ice. For analysis, the samples were thawed and kept at 4° C. immediately prior to use. Plasma (~0.2 mL) was clarified by addition of ice-cold methanol (1.5 mL) followed by centrifugation of the mixture (3 minutes, 20,000×g; 4° C.). The supernatant was evaporated to dryness using a rotary evaporator (Heidolph Instruments GMBH & Co, Schwabach, Germany) at a bath temperature of 35° C. The residue was re-suspended in HPLC mobile phase (1.2 mL), clarified (0.2 μm filter) and the sample (1 mL) injected via a 1 mL sample loop onto the HPLC. Samples were analyzed by radio-HPLC on an Agilent 1100 series HPLC system (Agilent Technologies, Stockport, UK) equipped with a γ-RAM Model 3 gamma-detector (IN/US Systems inc., Florida, USA) and Laura 3 software (Lablogic, Sheffield, UK) and UV (254 nm). A Waters βBondapak $C_{18}$ reverse-phase column (300 mm×7.8 mm) stationary phase was eluted with a mobile phase comprising of 67% water (0.1% TFA)/33% acetonitrile (0.1% TFA) delivered isocratically at 3 mL/min.

Example 11

PET Imaging Studies

Dynamic PET imaging scans were carried out on a dedicated small animal PET scanner, (Siemens Inveon PET module, Siemens Molecular Imaging Inc, UK) (Workman, P., et al., *Br J. Cancer.* 2010; 102:1555-1577; Leyton, J., et al., *Cancer Res.* 2006; 66:7621-7629). Briefly, tail veins were cannulated under general anesthesia (isofluorane). The animals were placed within a thermostatically controlled environment within the scanner; heart rate was monitored throughout the study. The mice were injected with 3.0-3.7 MBq of the different radiolabeled compounds and dynamic PET-CT scans were acquired in list-mode format over 60 min. In the case of FET-βAG-TOCA blocking studies were also done whereby radiotracer injection and imaging commenced 10 min after i.v. injection of 10 mg/kg unlabelled octreotide (Sigma) to mice; this dose of octreotide was ~100-fold higher than the equivalent dose of unlabelled FET-βAG-TOCA in the radiotracer injectate. The acquired data in all cases were sorted into 0.5-mm sinogram bins and 19 time frames (0.5×0.5×0.5 mm voxels; 4×15 s, 4×60 s, and 11×300 s) for image reconstruction. The image data-sets obtained were visualized and quantified using the Siemens Inveon Research Workplace software. Three-dimensional regions of interest (3D ROIs) were manually defined on five adjacent tumor, liver, kidney, muscle or urine/bladder regions (each 0.5 mm thickness). Data were averaged for tissues at each of the 19 time points to obtain time versus radioactivity curves (TACs). Radiotracer uptake for each tissue was normalized to injected dose and expressed as percent injected activity per mL of tissue (% ID/mL).

Example 12

Direct Counting of Tissue Radioactivity

After the 60 min PET scan, a part of the tumor tissue was obtained from mice after exsanguination via cardiac puncture under general isoflurane anesthesia. All samples were weighed and their radioactivity directly determined using a Cobra II Auto-gamma counter (formerly Packard Instruments Meriden CT USA) applying a decay correction. The results were expressed as a percentage of the injected dose per gram (% ID/g).

Example 13

Statistics

Statistical analyses were performed using the software GraphPad Prism, version 4.00 (GraphPad, San Diego, Calif.). Between-group comparisons were made using the nonparametric Mann-Whitney test. Two-tailed P value ≤0.05 were considered significant.
Results
Radiotracers. All radiotracers were successfully prepared with >98% radiochemical purity. The total synthesis time was ~1.5 h. The lipophilicity (Log D) of the radiotracers was measured using methods known in the art (Barthel, H., et al., *Br J. Cancer.* 2004; 90:2232-2242) and the measured Log D is shown in Table 6. Because the animals were scanned on different days, the mean specific radioactivity for each radiotracer is also presented (Table 6). Table 6. Comparison of tissue uptake of [$^{18}$F]-octreotate analogs in AR42J tumor xenografts growing in nude mice. Imaging data are presented for the 60 min time point together with data obtained from counting pieces of tissue directly in a γ-counter soon after the imaging study. In vivo FET-βAG-TOCA blocking studies were done after i.v. injection of unlabelled octreotide (10 mg/kg) to mice followed 10 min later by injection of the radiotracer. Data are mean±SE, n=3-6.

| Octreotate analog | Log D | Specific radio-activity (GBq/μmol)* | Tumor studied | Tumor radiotracer uptake at 60 min by imaging (% ID/ml) | Tumor radiotracer uptake after 60 min by γ-counting (% ID/g) |
|---|---|---|---|---|---|
| FET-G-PEG-TOCA | −2.68 | 4.8 | AR42J | 5.36 ± 0.45 | 8.29 ± 1.42 |
| FETE-PEG-TOCA | −2.77 | 5.9 | AR42J | 5.14 ± 0.40 | 9.78 ± 2.57 |
| FET-G-TOCA | −1.82 | 5.9 | AR42J | 11.0 ± 1.49 | 17.04 ± 2.76 |
| FETE-TOCA | −1.50 | 8.4 | AR42J | 6.11 ± 1.46 | 4.50 ± 1.51 |
| FET-βAG-TOCA | −2.06 | 3.9 | AR42J | 8.23 ± 2.02 | 11.58 ± 0.67 |
| FET-βAG-TOCA | −2.06 | 18.7 | HCT116 | 2.42 ± 0.35 | 0.52 ± 0.39 |
| FET-βAG-TOCA blocking | −2.06 | 11.2 | AR42J | 6.24 ± 0.64 | 3.93 ± 0.99 |
| FET-βAG-[W-c-(CTFTYC)K] | −1.14 | 12.3 | AR42J | 0.10 ± 0.05 | 0.22 ± 0.12 |
| [$^{18}$F]AlF-NOTA-OC | ND | 36.1 | AR42J | 6.43 ± 0.85 | 12.73 ± 0.05 |
| [$^{68}$Ga]DOTA-TATE | ND | ND | AR42J | 2.75 ± 0.11 | 3.78 ± 0.32 |

*Determined at the end of synthesis
ND: Not determined

In vitro sstr-subtype specificity. All the [$^{19}$F]fluoroethyl-triazole-[Tyr$^3$]octreotate analogs exhibited agonist activity on sstr-2 (FIG. 14), with the scrambled peptide, (FET-βAG-[W-c-(CTFTYC)K]), having expectedly poor affinity. The affinity of the ligands (EC$_{50}$) ranged between 4 and 19 nM (versus somatostatin at 5.6 nM) with the polyethylene glycol (PEG)-TOCA analogs showing the lowest affinity to sstr-2. Antagonistic activity was not evaluated because the analogs possessed significant agonist activity. None of the compounds exhibited detectable activity against sstr-3. All [$^{19}$F] fluoroethyltriazole-[Tyr$^3$]octreotate analogs except the scrambled peptide showed detectable activity against sstr-4 but the affinity was very poor 5.4 mM). In vitro studies revealed that the triazole analogs had high selective affinity to sstr-2 with half-maximal agonist activity in the calcium flux assay for this G-protein coupled receptor (EC$_{50}$) ranging from 4 to 19 nM, compared to the scrambled peptide, which had a low affinity.

Figure 15A:
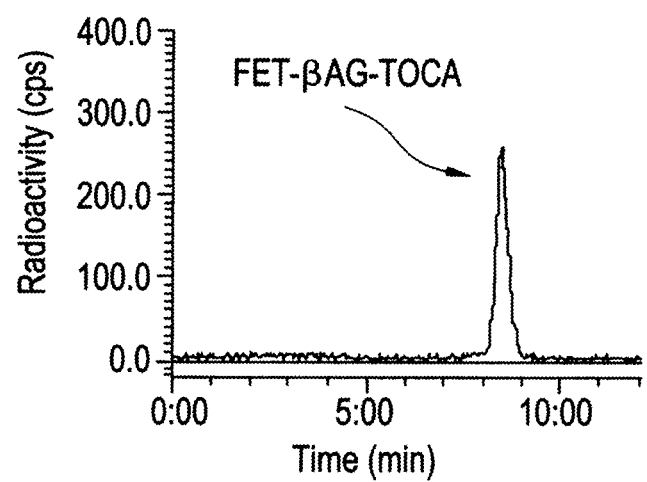
FIG. 15. RadioHPLC chromatography of [$^{18}$F]-FET-βAG-TOCA. (a) Reference standard showing analyte retention time at 8.47 min and (b) typical plasma extract obtained 30 min after injection of the radiotracer into mice, indicating a stable radiotracer.
Figure 15B:
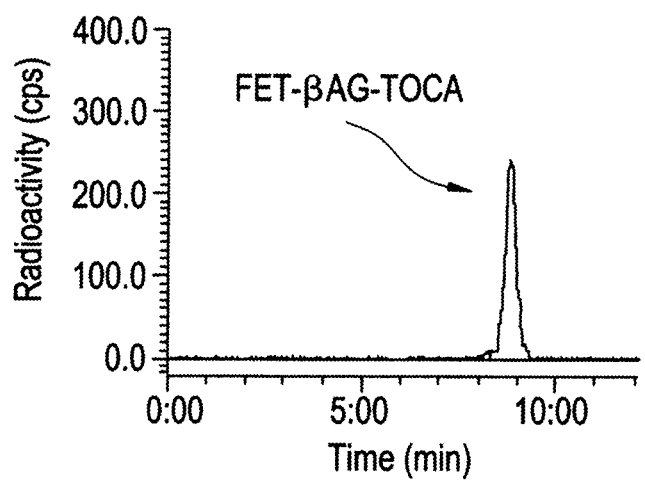

FET-βAG-TOCA is stable in vivo. The in vivo stability of FET-βAG-TOGA was examined. Typical radio-chromatograms of dose solution and 30 min mouse plasma are shown in FIG. 15. No metabolites of FET-βAG-TOGA were seen; only intact parent tracer was found. The combined effect of high binding affinity for sstr-receptor and rapid washout from non-target tissue produced high-contrast PET images in vivo, demonstrated for FET-βAG-TOGA in FIG. 16. The increasing tumor time versus activity curves of FET-βAG-TOGA derived from the in vivo dynamic PET image data (FIG. 17) reflected the high selective binding of FET-βAG-TOCA. The radiotracer was metabolically stable in mice and had low bone uptake indicating no significant defluorination.

Figure 16A:
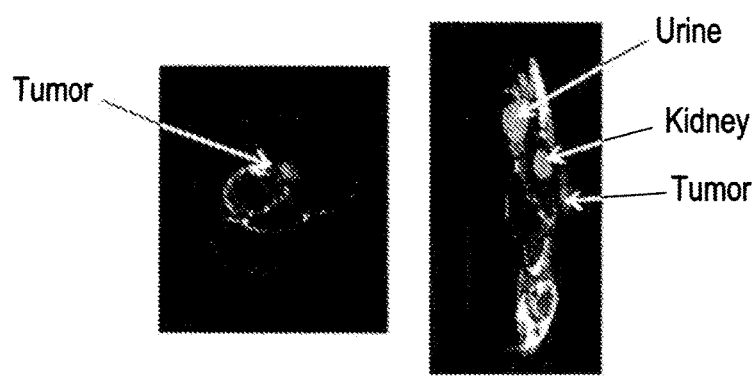
FIG. 16. PET-CT images showing localization of (a) [$^{18}$F]-FET-βAG-TOCA and (b) the scrambled peptide FET-βAG-[W-c-(CTFTYC)K] in tumors, kidney, and bladder of AR42J tumor bearing mice. Transverse and sagittal static (30-60 min fused; 0.5 mm slice) images are shown.
Figure 16B:
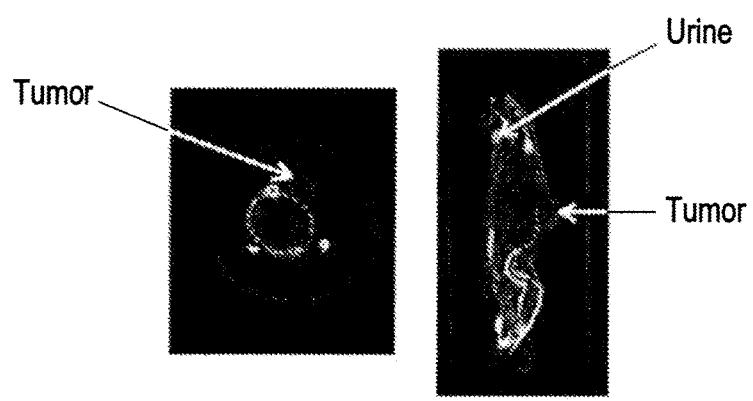
Figure 18A:
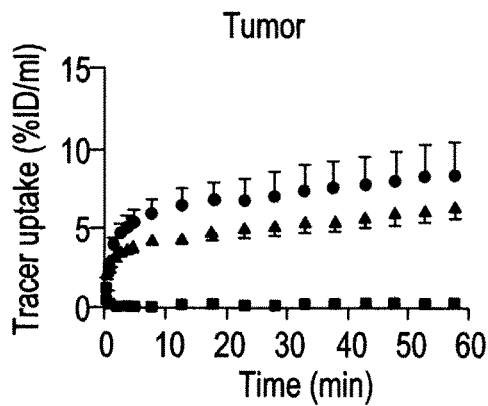
FIG. 18. Specificity of FET-βAG-TOCA localization in the AR42J xenograft model. Kinetics of [$^{18}$F]-FET-βAG-TOCA and effect of saturating receptor binding sites with excess cold unlabelled octreotide are shown. Blocking studies were carried out by injecting octreotide (10 mg/kg; i.v.) 10 min before i.v. injection of [$^{18}$F]-FET-βAG-TOCA. Dynamic imaging was performed over 60 min. Tissue radiotracer uptake values are expressed as % injected dose/mL of tissue. The graphs also illustrate pharmacokinetics of the scrambled peptide, FET-βAG-[W-c-(CTFTYC)K] in the same mouse model. Values represent the mean±SEM (n=3-5); upper and lower bars are used for clarity. Symbols are (•) FET-βAG-TOCA in octreotide naïve mice, (▲) FET-βAG-TOCA in mice pre-dosed with 10 mg/kg unlabelled octreotide, and (■) FET-βAG-[W-c-(CTFTYC)K] in octreotide naïve mice.
Figure 18B:
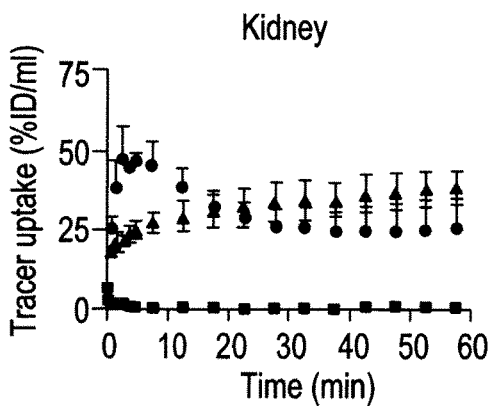
Figure 18C:
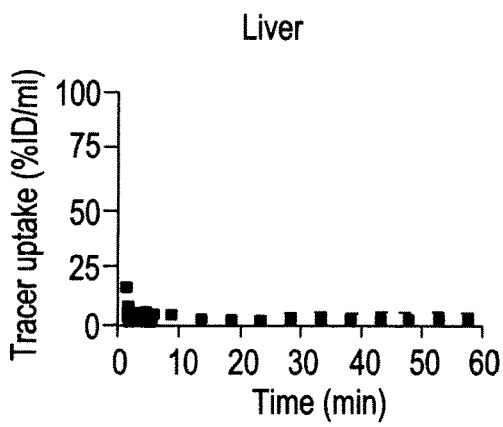
Figure 18D:
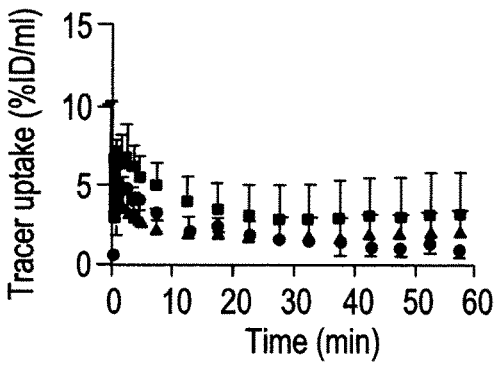
Figure 18E:
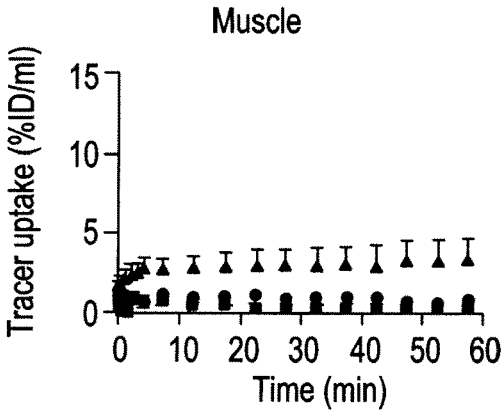
Figure 18F:
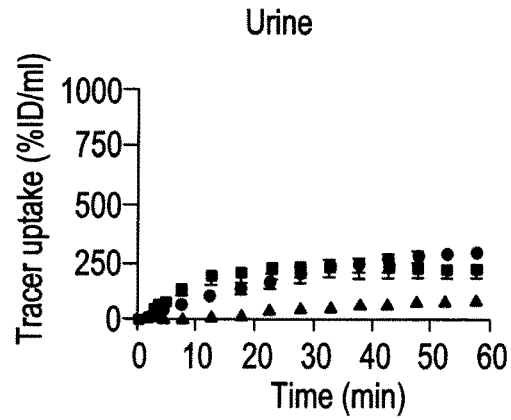

Pharmacokinetics and in vivo tumor localization of [$^{18}$F] fluoroethyltriazole-[Tyr$^3$]octreotate analogs. Given the high affinity and systemic stability of FET-βAG-TOGA, it was reassuring to observe good localization of the radiotracer in tumor. FIG. 16a shows typical transverse and sagittal PET image slices through sstr-2 expressing AR42J tumor bearing mice demonstrating localization of FET-βAG-TOGA in tumor, kidney and bladder/urine with high signal-to-background contrast. In contrast, no radiotracer localization was seen in tumor and kidneys of the mice when the scrambled peptide FET-βAG-[W-c-(CTFTYC)K] was injected (FIG. 16b). In this case, tracer localization was seen mainly in brain, urine, liver and intestines (data not shown). The comparative pharmacokinetics of all [$^{18}$F]fluoroethyltriazole-[Tyr$^3$]octreotate analogs in tumor, kidney, liver, muscle and bladder/urine are shown in FIG. 17. Radiotracer uptake in the AR42J tumor was characterized by a rapid increase over the entire scanning period of 60 min. FET-G-TOGA had the highest tumor uptake followed by FET-βAG-TOGA, which had higher or comparable uptake as [$^{18}$F]-AIF-NOTA-OC. These tracers were superior to the clinical radiotracer, [$^{68}$Ga]-DOTATATE, with respect to tumor uptake (Table 6). PEG-linkers, embodied within the structures of FET-G-PEG-TOCA and FETE-PEG-TOGA, reduced tumor uptake (FIG. 17; Table 6). Non-specific uptake in liver was in general low (<7% ID/mL) with FET-βAG-TOGA showing the lowest liver uptake; FET-G-TOGA and FETE-PEG-TOGA showed the highest liver uptake. The PEG-TOGA analogs had the highest urinary clearance in keeping with their lower lipophilicity. Radiotracer kinetic profiles in kidney which also expresses sstr- (Bates, C M, et al., Kidney Int. 2003; 63:53-63) were different from those in tumors, however, the magnitude of uptake was highest for the two radiotracers, FET-βAG-TOGA and FET-G-TOGA; [$^{18}$F]-AIF-NOTA-octreotide had relatively low kidney uptake. The mean muscle uptake was <3% ID/mL for all radiotracers. Radiotracer uptake in the bone was low for all the analogs indicating little/no defluorination. We compared the uptake of the radiotracers in the imaging studies to direct tissue counting. The profiles were generally in agreement, but the magnitude was higher for direct counting, consistent with partial volume averaging. Direct radioactivity determination (gamma counting) of only a part of the tissue compared to sampling of the whole tumor in the case of imaging could also have led to systematic differences.

The uptake of FET-βAG-TOCA is specific. Given the high tumor uptake of the radiotracers, we next assessed the specificity of uptake in vivo using FET-βAG-TOGA as the prototypical [$^{18}$F]-fluoroethyltriazole-[Tyr$^3$]octreotate. We demonstrated that radiotracer uptake was specific: i) In keeping with the poor affinity for sstr-2, the radiolabeled scrambled peptide, (FET-βAG-[W-c-(CTFTYC)K]), did not show detectable tumor uptake in the AR42J model in vivo (FIG. 18). -FET-βAG-[W-c-(CTFTYC)K] uptake was also low in the high sstr-expressing normal tissue (kidneys), and uptake was higher in liver compared to FET-βAG-TOGA. ii) To show that the tumor uptake of radiotracer was receptor-mediated, blocking studies were conducted by pre-injecting mice with excess unlabelled octreotide (100-fold molar equivalent) to saturate sstr-binding sites. This resulted in a 2-fold (by direct counting) lower uptake of FET-βAG-TOCA in AR42J xenografts (FIG. 18; Table 6). Following blocking with unlabelled octreotide, kidney (early time points only), muscle and to a smaller extent liver radioactivity concentrations increased and urine radioactivity decreased (FIG. 18). iii) Further evidence for the specificity of FET-βAG-TOGA uptake was provided by the low uptake in low sstr-expressing HCT116 xenografts compared to the AR42J xenografts (Table 6).

Figure 14:
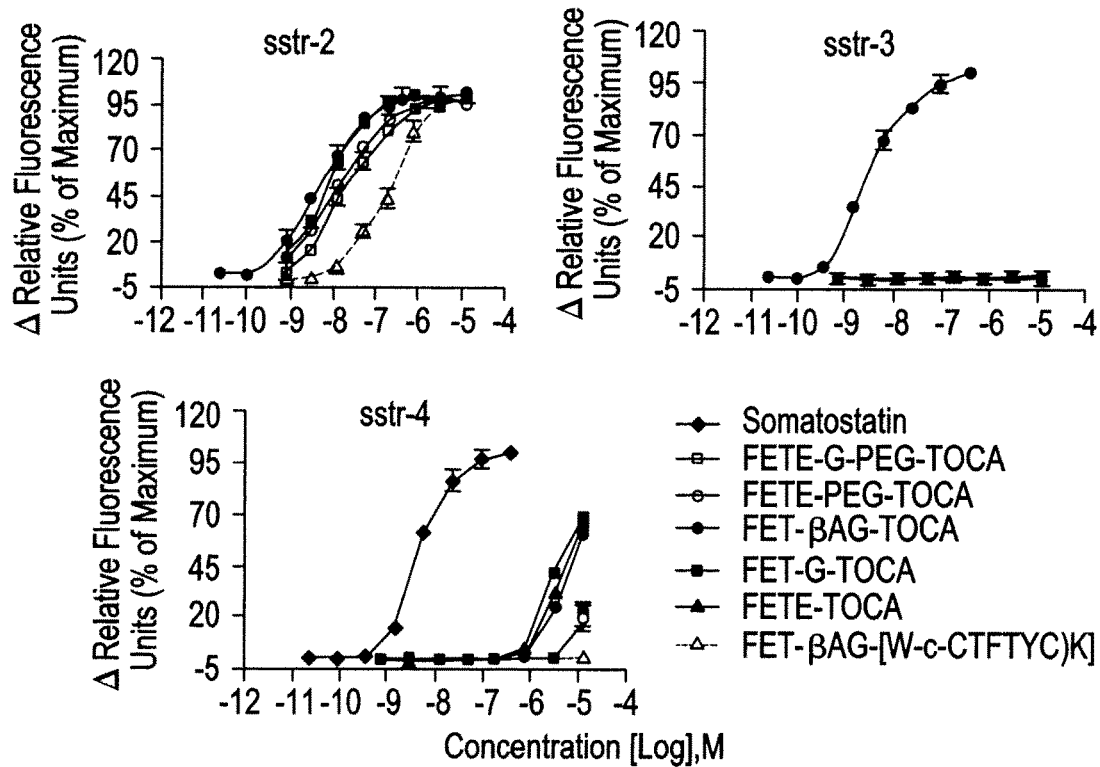
FIG. 14 depicts affinity profiles of different [$^{18}$F]ethyltriazole-[Tyr$^3$]octreotate analogs for somatostatin receptor subtypes sstr-2, 3 and 4 determined using a calcium flux fluorometric imaging plate reader (FLIPR) assay (see Examples). The activation of calcium flux by [$^{18}$F]ethyltriazole-[Tyr$^3$]octreotate analogs in sstr-2, 3 or 4—expressing cells that were pre-loaded with a calcium dye was assessed at different concentrations; the assay was performed in duplicate. Fluorescence output was measured and data expressed as % maximal fluorescence signal. The half-maximal receptor activation for the various agonist ligands is summarized. ND=not determined due to lack of activity.

Interestingly, the tumor uptake for FET-G-TOGA and FET-βAG-TOGA compounds ranked amongst the highest reported to date and were higher than that of [$^{68}$Ga]-DOTATATE (Table 6), which is used clinically. Similarly the tumor uptake of the two [$^{18}$F]-fluoroethyltriazole-[Tyr]$^3$-octreotate analogs was significantly higher than those reported for [$^{111}$In]-DTPA-octreotide by Froidevaux et al., (3.03±0.26% ID/g) in the same tumor model (Froidevaux, S., et al., Endocrinology. 2000; 141:3304-3312). The tracers also showed similar or higher uptake compared to [$^{18}$F]-AIF-NOTA-OC. In contrast to the high tumor uptake of FET-G-TOCA and FET-βAG-TOCA, the two PEGylated analogs showed lower tumor (and kidney) uptake. This was an unexpected finding given that PEGylation of peptides often increases the half-life and generally reduces the overall clearance from the body (Veronese, F. M., et al., Drug Discov Today. 2005; 10:1451-1458). This finding may be explained in part by the fact that one of the properties of PEGylation is also to make the molecule more water soluble (Veronese, F. M., et al., BioDrugs. 2008; 22:315-329), supporting a faster clearance from the circulation compared to the less hydrophilic non-PEGylated analogs; supported by high urinary clearance (FIG. 17f). The low uptake of the PEG-TOGA analogs could also be explained by their lower in vitro affinity (FIG. 14).

It was predicted that tissues such as liver and muscle that lacked receptor expression (Reynaert, H., et al., Gut. 2004; 53:1180-1189) will show low uptake of the radiotracers. The PEG-TOGA analogs showed lower non-target tissues uptake. It is likely that the higher hydrophilicity resulting from PEGylation in this series leads to more rapid elimination from non-target tissues. The time course from the PET studies allowed this effect to be quantified. Interestingly, FET-βAG-TOGA with intermediate hydrophilicity compared to the PEGylated analogs (Table 6), showed similar low uptake in non-target tissues, including liver and muscle. This is a positive attribute of FET-βAG-TOGA that was not realized in FET-G-TOGA, which had the highest tumor uptake.

Imaging

A triazole linked [Tyr³]octreotate analogue or a 2-[¹⁸F] fluoroethyl triazole linked [Tyr³]octreotate analogue of the invention can be used as a radiotracer or an imaging agent for those disease states or tumors that exhibit increased or high levels of somatostatin receptors.

In one embodiment, a 2-[¹⁸F]fluoroethyl triazole linked [Tyr³]octreotate analogue of the invention can be used as a PET radiotracer for those disease states or tumors that exhibit increased or high levels of somatostatin receptors. In one embodiment, a 2-[¹⁸F]fluoroethyl triazole linked [Tyr³] octreotate analogue of the invention can be used as a PET radiotracer that is useful for the in vivo detection of neuroendocrine tumours which are known to express increased levels of somatostatin receptors. In one embodiment, a 2-[¹⁸F]fluoroethyl triazole linked [Tyr³]octreotate analogue of the invention can be used as a PET radiotracer that is useful for the detection of lung tumors that express high levels of somatostatin receptors.

Therefore in one aspect, the present invention provides a PET imaging method to determine the distribution and/or the extent of a disease state or a tumor that exhibits increased or high levels of somatostatin receptors, wherein said method comprises:
 i) administering to said subject a 2-[¹⁸F]fluoroethyl triazole linked [Tyr³]Octreotate analogue(s) of the invention as described herein;
 ii) allowing said 2-[¹⁸F]fluoroethyl triazole linked [Tyr³] Octreotate analogue(s) of the invention to bind to the somatostatin receptor(s) in said subject;
 iii) detecting signals emitted by the ¹⁸F comprised in said 2-[¹⁸F]fluoroethyl triazole linked [Tyr³]Octreotate analogue(s) of the invention; and
 iv) generating an image representative of the location and/or amount of said signals.

The method optionally further comprises the step of determining the distribution and extent of the disease state in said subject wherein said distribution and extent of disease state is directly correlated with said signals.

In another aspect, the present invention provides a PET imaging method to determine the distribution and/or the extent of a or multiple neuroendocrine tumors in a subject, wherein said method comprises:
 i) administering to said subject a 2-[¹⁸F]-fluoroethyl triazole linked [Tyr³]Octreotate analogue(s) of the invention as described herein;
 ii) allowing said 2-[¹⁸F]-fluoroethyl triazole linked [Tyr³] Octreotate analogue(s) of the invention to bind to the somatostatin receptor(s) on the surface of said neuroendocrine tumour(s) in said subject;
 iii) detecting signals emitted by the 18F comprised in said 2-[¹⁸F]fluoroethyl triazole linked [Tyr3]Octreotate analogue(s) of the invention; and
 iv) generating an image representative of the location and/or amount of said signals.

The method optionally further comprises the step of determining the distribution and extent of neuroendocrine tumour(s) in said subject wherein said distribution and extent of neuroendocrine tumour(s) is directly correlated with said signals.

In another aspect, the present invention provides a PET imaging method to determine the distribution and/or the extent of a or multiple lung tumors in a subject, wherein said method comprises:
 i) administering to said subject a 2-[¹⁸F]fluoroethyl triazole linked [Tyr³]Octreotate analogue(s) of the invention as described herein;
 ii) allowing said 2-[¹⁸F]fluoroethyl triazole linked [Tyr³] Octreotate analogue(s) of the invention to bind to the somatostatin receptor(s) on the surface of the lung tumour(s) in said subject;
 iii) detecting signals emitted by the ¹⁸F comprised in said 2-[¹⁸F]fluoroethyl triazole linked [Tyr³]Octreotate analogue(s) of the invention; and
 iv) generating an image representative of the location and/or amount of said signals.

The method optionally further comprises the step of determining the distribution and extent of lung tumour(s) in said subject wherein said distribution and extent of lung tumour(s) is directly correlated with said signals.

The step of "administering" the 2-[¹⁸F]fluoroethyl triazole linked [Tyr³]octreotate analogue of the invention is preferably carried out parenterally, and most preferably intravenously. The intravenous route represents the most efficient way to deliver the 2-[¹⁸F]-fluoroethyl triazole linked [Tyr³]octreotate analogue of the invention throughout the body of the subject. Intravenous administration neither represents a substantial physical intervention nor a substantial health risk to the subject. The 2-[¹⁸F]fluoroethyl triazole linked [Tyr³]octreotate analogue of the invention is preferably administered as the radiopharmaceutical composition of the invention, as defined herein. The administration step is not required for a complete definition of the PET imaging method of the invention. As such, the PET imaging method of the invention can also be understood as comprising the above-defined steps (ii)-(v) carried out on a subject to whom the 2-[¹⁸F]fluoroethyl triazole linked [Tyr³]octreotate analogue of the invention has been pre-administered.

Following the administering step and preceding the detecting step, the 2-[¹⁸F]-fluoroethyl triazole linked [Tyr³] octreotate analogue of the invention is allowed to bind to somatostatin receptor(s). For example, when the subject is an intact mammal, the 2-[¹⁸F]-fluoroethyl triazole linked [Tyr³]octreotate analogue of the invention will dynamically move through the mammal's body, coming into contact with various tissues therein. Once the 2-[¹⁸F]-fluoroethyl triazole linked [Tyr³]octreotate analogue of the invention comes into contact with somatostatin receptor(s), a specific interaction takes place such that clearance of the 2-[¹⁸F]-fluoroethyl triazole linked [Tyr³]octreotate analogue of the invention from tissue with somatostatin receptor(s) takes longer than from tissue without, or with less somatostatin receptor(s). A certain point in time will be reached when detection of 2-[¹⁸F]fluoroethyl triazole linked [Tyr³]octreotate analogue of the invention specifically bound to somatostatin receptor(s) is enabled as a result of the ratio between PET radiotracer bound to tissue with somatostatin receptor(s) versus that bound in tissue without, or with less somatostatin receptor(s).

The "detecting" step of the method of the invention involves detection of signals emitted by the ¹⁸F comprised in the 2-[¹⁸F]fluoroethyl triazole linked [Tyr³]octreotate analogue of the invention by means of a detector sensitive to said signals, i.e. a PET camera. This detection step can also be understood as the acquisition of signal data.

The "generating" step of the method of the invention is carried out by a computer which applies a reconstruction algorithm to the acquired signal data to yield a dataset. This dataset is then manipulated to generate images showing the location and/or amount of signals emitted by the $^{18}$F. The signals emitted directly correlate with the expression of somatostatin receptor(s) such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human. The in vivo imaging method may be used to study somatostatin receptor(s) in healthy subjects, or in subjects known or suspected to have a pathological condition associated with abnormal expression of somatostatin receptor(s).

In an alternative embodiment, the PET imaging method of the invention may be carried out repeatedly during the course of a treatment regimen for said subject, said regimen comprising administration of a drug to combat a neuroendocrine tumor. For example, the PET imaging method of the invention can be carried out before, during and after treatment with a drug to combat a neuroendocrine tumor. In this way, the effect of said treatment can be monitored over time. PET is particularly well-suited to this application as it has excellent sensitivity and resolution, so that even relatively small changes in a lesion can be observed over time, a particular advantage for treatment monitoring.

All patents, journal articles, publications and other documents discussed and/or cited above are hereby incorporated by reference.

What is claimed is:

1. A 2-[$^{18}$F]fluoroethyl triazole linked [Tyr$^3$]octreotate analogue of formula (5b):

(5b)

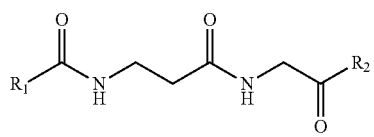

wherein:

R$_1$ is

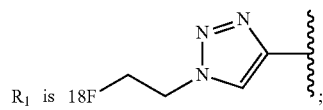

R$_2$ has the following structure:

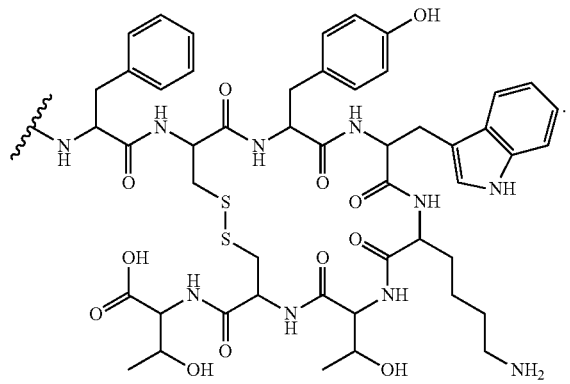 [SMILES: *NC(Cc1ccccc1)C(=O)NC1CSSCC(C(=O)NC(C(=O)O)C(C)O)NC(=O)C(C(C)O)NC(=O)C(CCCCN)NC(=O)C(Cc2c[nH]c3ccccc23)NC(=O)C(Cc2ccc(O)cc2)NC1=O]

2. The 2-[$^{18}$F]fluoroethyl triazole linked [Tyr$^3$]octreotate analogue according to claim 1, wherein, R$_2$ is:

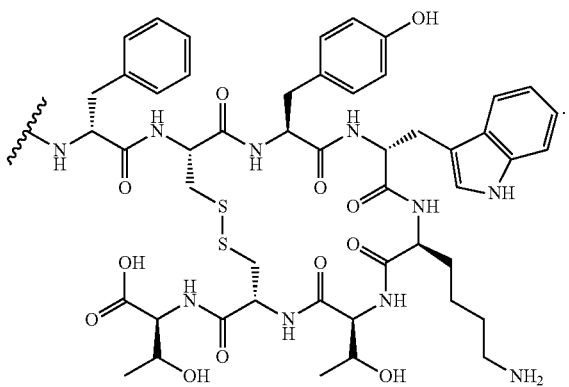

3. A pharmaceutical composition comprising at least one compound of claim 1 and a pharmaceutically acceptable carrier, excipient, or biocompatible carrier.

4. An alkyne linked [Tyr$^3$]octreotate analogue of formula (5a):

(5a)

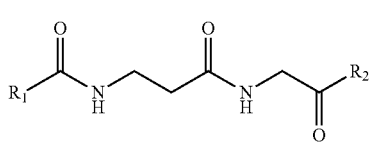

wherein:

R$_1$ is

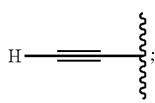

R$_2$ has the following structure:

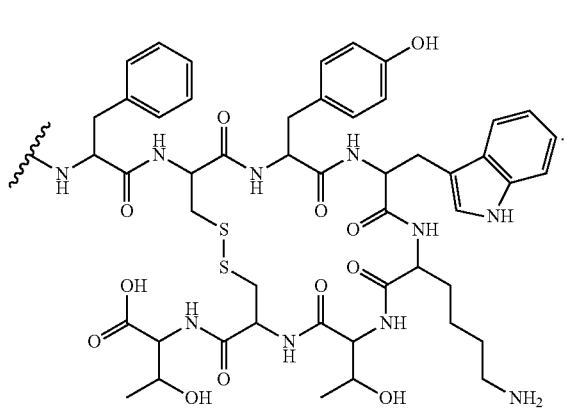 [SMILES: *NC(Cc1ccccc1)C(=O)NC1CSSCC(C(=O)NC(C(=O)O)C(C)O)NC(=O)C(C(C)O)NC(=O)C(CCCCN)NC(=O)C(Cc2c[nH]c3ccccc23)NC(=O)C(Cc2ccc(O)cc2)NC1=O]

—C≡C—,

5. The alkyne linked [Tyr³]octreotate analogue according to claim 4, wherein $R_2$ is:

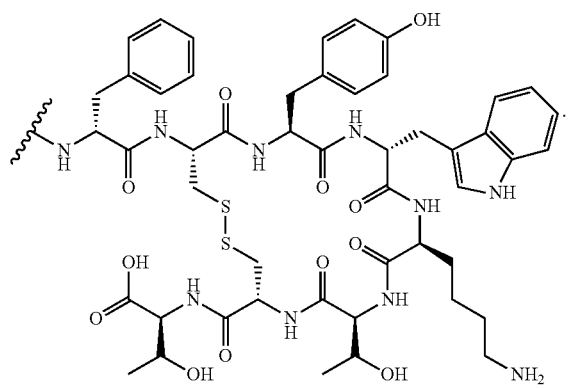 [SMILES: *N[C@H](Cc1ccccc1)C(=O)N[C@H]1CSSC[C@@H](C(=O)N[C@H](C(=O)O)C(C)O)NC(=O)[C@H](C(C)O)NC(=O)[C@H](CCCCN)NC(=O)[C@@H](Cc2c[nH]c3ccccc23)NC(=O)[C@H](Cc2ccc(O)cc2)NC1=O]

6. A method of making the 2-[¹⁸F]fluoroethyl triazole linked [Tyr³]octreotate analogue of claim 1; the method comprising the step of reacting an alkyne linked [Tyr³] Octreotate analogue having the formula (5a):

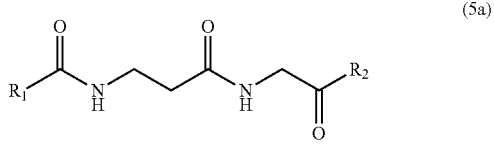

(5a)

with 2-[¹⁸F]Fluoroethylazide under copper catalyzed click chemistry conditions to form the corresponding 2-[¹⁸F] fluoroethyl triazole linked [Tyr³]octreotate analogue having the formula (5b) in claim 1; wherein:

$R_1$ in formula (5a) is

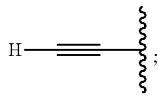

and
$R_2$ in formula (5a) has the following structure:

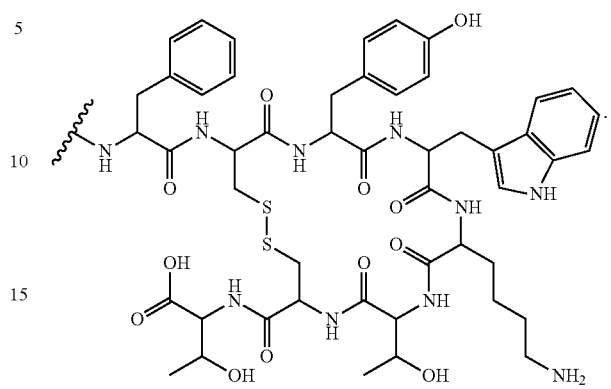

7. A method of imaging comprising the steps of administering a compound of claim 1 to a subject and detecting said compound in said subject.

8. The method of detecting neuroendocrine tumor(s) in vivo in a subject comprising the steps of:
(i) administering to said subject a compound of claim 1 or a pharmaceutical composition thereof;
(ii) allowing said compound or pharmaceutical composition thereof to bind to somatostatin receptor(s) found on the surface of the neuroendocrine tumour(s) in said subject;
(iii) detecting signals emitted by the radioisotope in said compound or pharmaceutical composition thereof on said neuroendocrine tumor(s) in said subject;
(iv) generating an image representative of the location and/or amount of said signals; and, optionally,
(v) determining the distribution and extent of said neuroendocrine tumour(s) in said subject.

9. The method of detecting lung tumor(s) in vivo in a subject comprising the steps of:
(i) administering to said subject a compound of claim 1 or a pharmaceutical composition thereof;
(ii) allowing said compound or pharmaceutical composition thereof to bind to somatostatin receptor(s) found on the surface of the lung tumour(s) in said subject;
(iii) detecting signals emitted by the radioisotope in said compound or pharmaceutical composition thereof on said lung tumor(s) in said subject;
(iv) generating an image representative of the location and/or amount of said signals; and, optionally,
(v) determining the distribution and extent of said lung tumour(s) in said subject.

* * * * *